(12) United States Patent
Dodd et al.

(10) Patent No.: US 9,968,700 B2
(45) Date of Patent: May 15, 2018

(54) MICROFLUIDIC DELIVERY SYSTEM AND METHOD

(71) Applicants: STMicroelectronics, Inc., Coppell, TX (US); STMicroelectronics S.r.l., Agrate Brianza (IT); STMicroelectronics International N.V., Schiphol (NL)

(72) Inventors: Simon Dodd, West Linn, OR (US); Joseph Edward Scheffelin, San Diego, CA (US); Dave S. Hunt, San Diego, CA (US); Timothy James Hoekstra, Escondido, CA (US); Faiz Sherman, Mason, OH (US); Stephan Gary Bush, Liberty Township, OH (US)

(73) Assignees: STMICROELECTRONICS, INC., Coppell, TX (US); STMICROELECTRONICS S.R.L., Agrate Brianza (IT); STMICROELECTRONICS INTERNATIONAL N.V., Schiphol (NL)

( * ) Notice: Subject to any disclaimer, the term of this patent is extended or adjusted under 35 U.S.C. 154(b) by 20 days.

(21) Appl. No.: 14/975,200

(22) Filed: Dec. 18, 2015

(65) Prior Publication Data

US 2016/0101429 A1   Apr. 14, 2016

Related U.S. Application Data

(63) Continuation-in-part of application No. 14/311,150, filed on Jun. 20, 2014.

(51) Int. Cl.
*A61L 9/03* (2006.01)
*B05B 17/06* (2006.01)
(Continued)

(52) U.S. Cl.
CPC ........ *A61L 9/03* (2013.01); *A61L 2/00* (2013.01); *A61L 9/00* (2013.01); *B05B 17/0684* (2013.01)

(58) Field of Classification Search
CPC ............ B05B 17/0684; B05B 17/0646; B05B 11/309; B05B 17/0607; B05B 17/0638; B05B 17/0669; B05B 1/14; B05B 1/26; B05B 7/0408; A61L 9/14; A61L 9/00; A61L 2/00; A61L 9/03; A61L 9/015;
(Continued)

(56) References Cited

U.S. PATENT DOCUMENTS 6,273,553 B1 *  8/2001  Kim ................. B05B 17/04
                                          347/48
7,726,303 B2 *  6/2010  Tyvoll ............. A61M 15/025
                                          128/200.21
(Continued)

*Primary Examiner* — Arthur O Hall
*Assistant Examiner* — Juan C Barrera
(74) *Attorney, Agent, or Firm* — Seed Intellectual Property Law Group LLP

(57) ABSTRACT

One or more embodiments are directed to a microfluidic delivery system that dispenses a fluid. The microfluidic delivery system may be provided in a variety of orientations. In one embodiment, the microfluidic delivery system is vertical so that fluid being expelled opposes gravity. In another embodiment, the microfluidic delivery system is orientated sideways so that fluid being expelled has a horizontal component. In yet another embodiment, the microfluidic delivery system faces downward.

29 Claims, 18 Drawing Sheets

(51) Int. Cl.
  *A61L 2/00*     (2006.01)
  *A61L 9/00*     (2006.01)

(58) Field of Classification Search
  CPC .......... A61L 9/037; A61L 9/122; A61L 9/127;
      A61L 2209/111; A61L 2209/12; A61L
      2209/131; A61L 9/02; A61L 9/035; A61L
      9/04; A61L 9/042; A61L 9/048; A61L
      9/125; A01M 1/2077; A01M 1/2033;
      A01M 1/205; A01M 1/2044; A01M
      1/2038; A01M 1/2055; A01M 1/2072;
      A61M 15/025; A61M 11/005; A61M
      11/007; A61M 11/041; A61M 11/042;
      A61M 15/0065; A61M 15/0066; A61M
      15/008; A61M 15/0085; A61M 16/0833;
      A61M 16/1075; A61M 16/109; A61M
      16/142; A61M 16/147; A61M 16/16;
      A61M 2205/3368; A61M 2205/3653
  USPC .......... 239/44–51.5, 13, 135, 128, 136, 552,
      239/596, 601, 548, 311, 324, 386, 394,
      239/395; 156/345.11, 345.17
  See application file for complete search history.

(56) References Cited

U.S. PATENT DOCUMENTS

| | | | |
|---|---|---|---|
| 7,920,777 B2* | 4/2011 | Rabin | A01M 1/2077 |
| | | | 122/366 |
| 8,287,102 B2* | 10/2012 | Tseng | B41J 2/1404 |
| | | | 347/10 |
| 2003/0063162 A1* | 4/2003 | Yoshihira | B41J 2/14064 |
| | | | 347/65 |
| 2003/0193544 A1* | 10/2003 | Eguchi | B41J 2/04505 |
| | | | 347/48 |
| 2004/0263578 A1* | 12/2004 | Lee | B41J 2/14137 |
| | | | 347/65 |
| 2005/0001050 A1* | 1/2005 | Takagi | B01L 3/0268 |
| | | | 239/4 |
| 2007/0008380 A1 | 1/2007 | Ushinohama et al. | |
| 2009/0224064 A1* | 9/2009 | Brodbeck | A01M 1/2077 |
| | | | 239/6 |
| 2011/0072711 A1* | 3/2011 | Black | A01M 1/2033 |
| | | | 43/123 |
| 2011/0315786 A1* | 12/2011 | Kambayashi | B05B 17/0684 |
| | | | 239/102.2 |
| 2012/0093491 A1 | 4/2012 | Browder et al. | |

* cited by examiner

MICROFLUIDIC DELIVERY SYSTEM AND METHOD

BACKGROUND

Technical Field

Embodiments are directed to microfluidic delivery systems that utilize refillable cartridges and methods of making and using the same.

Description of the Related Art

It is often desired to provide scent dispersal systems in a home, particularly in a workroom or bathroom to improve the air quality and comfort of people in the home. Scent dispersal systems provide a scented fluid into the air for scenting an environment. Scent dispersal systems usually do not provide adequate control of the scented fluid being dispersed. Typically, scent dispersal systems disperse scented fluid by evaporation. As the scented fluid evaporates into the air, the scent disperses in the environment. These systems, however, do not provide consistent quality of the scented fluid over a period of time. For instance, the scented fluid often changes in consistency if allowed to evaporate for thirty days or more. Additionally, a significant amount of the scented fluid is wasted due to the evaporation. Although some systems may include a hot plate to control the rate of evaporation, these systems still use evaporation for dispersing the sent, thereby limiting the quality of systems.

BRIEF SUMMARY

One or more embodiments are directed to a microfluidic delivery system that dispenses a fluid. The microfluidic delivery system includes a microfluidic refill cartridge in a variety of orientations. In one embodiment, the microfluidic refill cartridge is vertical so that fluid being expelled opposes gravity. In another embodiment, the microfluidic refill cartridge is orientated sideways so that fluid being expelled has a horizontal component. In yet another embodiment, the microfluidic refill cartridge faces downward.

One embodiment is directed to a microfluidic delivery system that dispenses a fluid in a direction that, at least in part, opposes gravity. In one embodiment, the microfluidic delivery system includes a microfluidic refill cartridge that is configured to be placed in a housing. The microfluidic refill cartridge includes at least one nozzle that faces upward or off to a side. The microfluidic refill cartridge includes a fluid transport member that allows fluid to travel upward from a fluid reservoir in opposition to gravity. A fluid path is located above the fluid transport member placing an end of the fluid transport member in fluid communication with a chamber and a nozzle. In response to the microfluidic delivery system receiving an electrical signal, an ejection element, such as a heating element, piezoelectric element, or ultrasonic ejection element, is configured to cause fluid to be expelled through the nozzle. In response to the fluid being expelled from the nozzle, fluid may be pulled up through the fluid transport member and through the fluid path to refill the chamber.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

DETAILED DESCRIPTION

Figure 1:
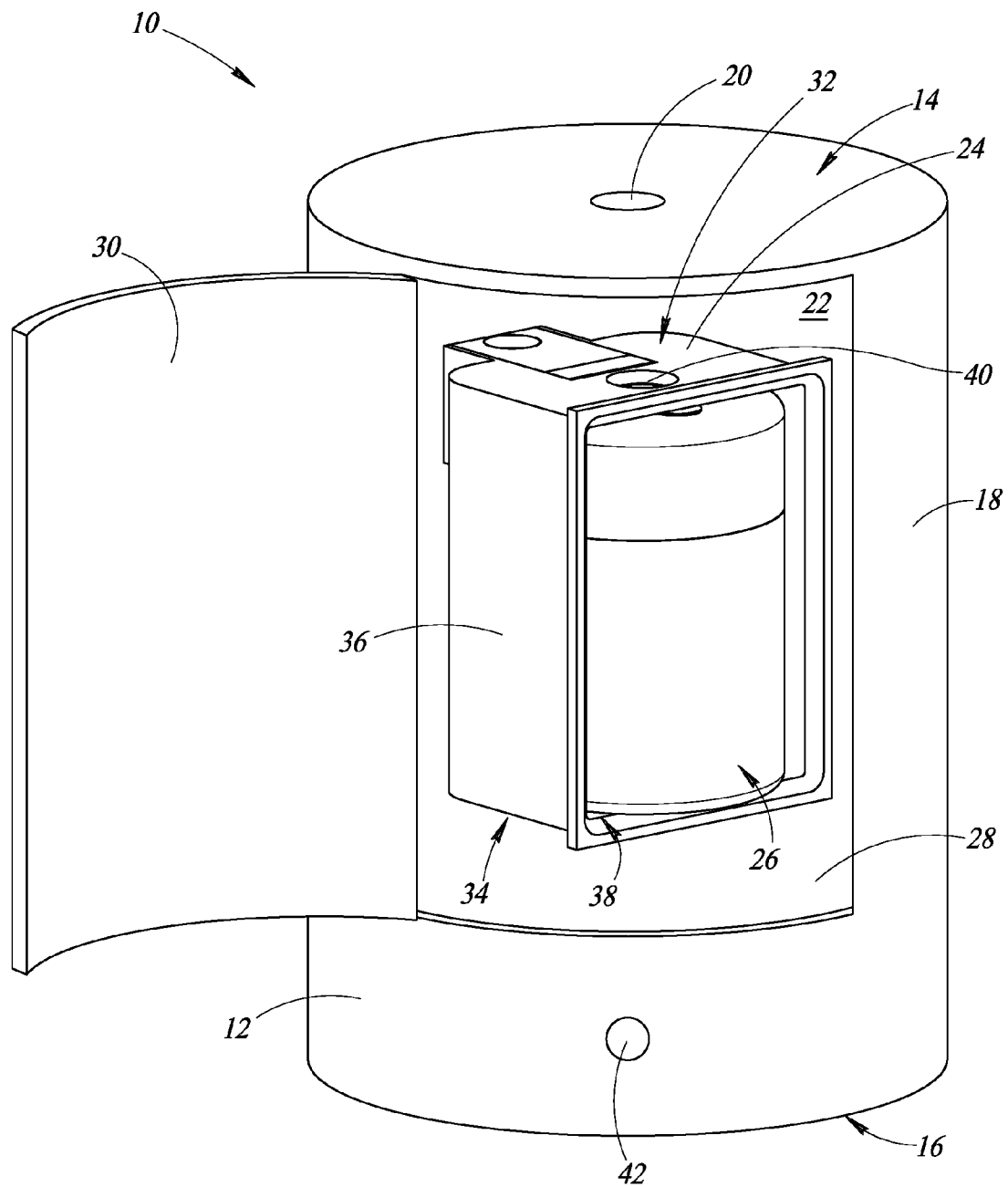
FIG. 1 is a schematic isometric view of a microfluidic delivery system in accordance with one embodiment.

FIG. 1 illustrates a microfluidic delivery system 10 in accordance with one embodiment of the disclosure. The microfluidic delivery system 10 includes a housing 12 having an upper surface 14, a lower surface 16, and a body portion 18 between the upper and lower surfaces. The upper surface of the housing 12 includes a first hole 20 that places an environment external to the housing 12 in fluid communication with an interior portion 22 of the housing 12. The interior portion 22 of the housing 12 includes a holder member 24 that holds a removable microfluidic refill cartridge 26. As will be explained below, the microfluidic delivery system 10 is configured to use thermal energy to deliver fluid from within the microfluidic refill cartridge 26 to an environment external to the housing 12.

Access to the interior portion 22 of the housing is provided by an opening 28 in the body portion 18 of the housing 12. The opening 28 is accessible by a cover or door 30 of the housing 12. In the illustrated embodiment, the door 30 rotates to provide access to the opening 28. Although the opening and door are located on the body portion of the housing, it is to be appreciated that the opening and door may also be located on the upper surface and the lower surface of the housing. Furthermore, it is to be appreciated that in other embodiments, the housing has two or more separable parts for providing access to the interior portion.

The holder member 24 includes an upper surface 32 and a lower surface 34 that are coupled together by one or more sidewalls 36 and has an open side 38 through which the microfluidic refill cartridge 26 can slide in and out. The upper surface 32 of the holder member includes an opening 40 that is aligned with the first hole 20 of the housing 12.

The holder member 24 holds the microfluidic refill cartridge 26 in position when located therein. In one embodiment, the holder member 24 elastically deforms, thereby gripping the microfluidic refill cartridge 26 in place when located in the holder member. In another embodiment, the holder member 24 includes a locking system (not shown) for holding the microfluidic refill cartridge in place. In one embodiment, the locking system includes a rotatable bar that extends across the open side of the holder member to hold the microfluidic refill cartridge in place.

The housing 12 includes conductive elements (not shown) that couple electrical components throughout the system as is well known in the art. The housing 12 may further include connection elements for coupling to an external or internal power source. The connection elements may be a plug configured to be plugged into an electrical outlet or battery terminals. The housing 12 may include a power switch 42 on a front of the housing 12.

Figure 2A:
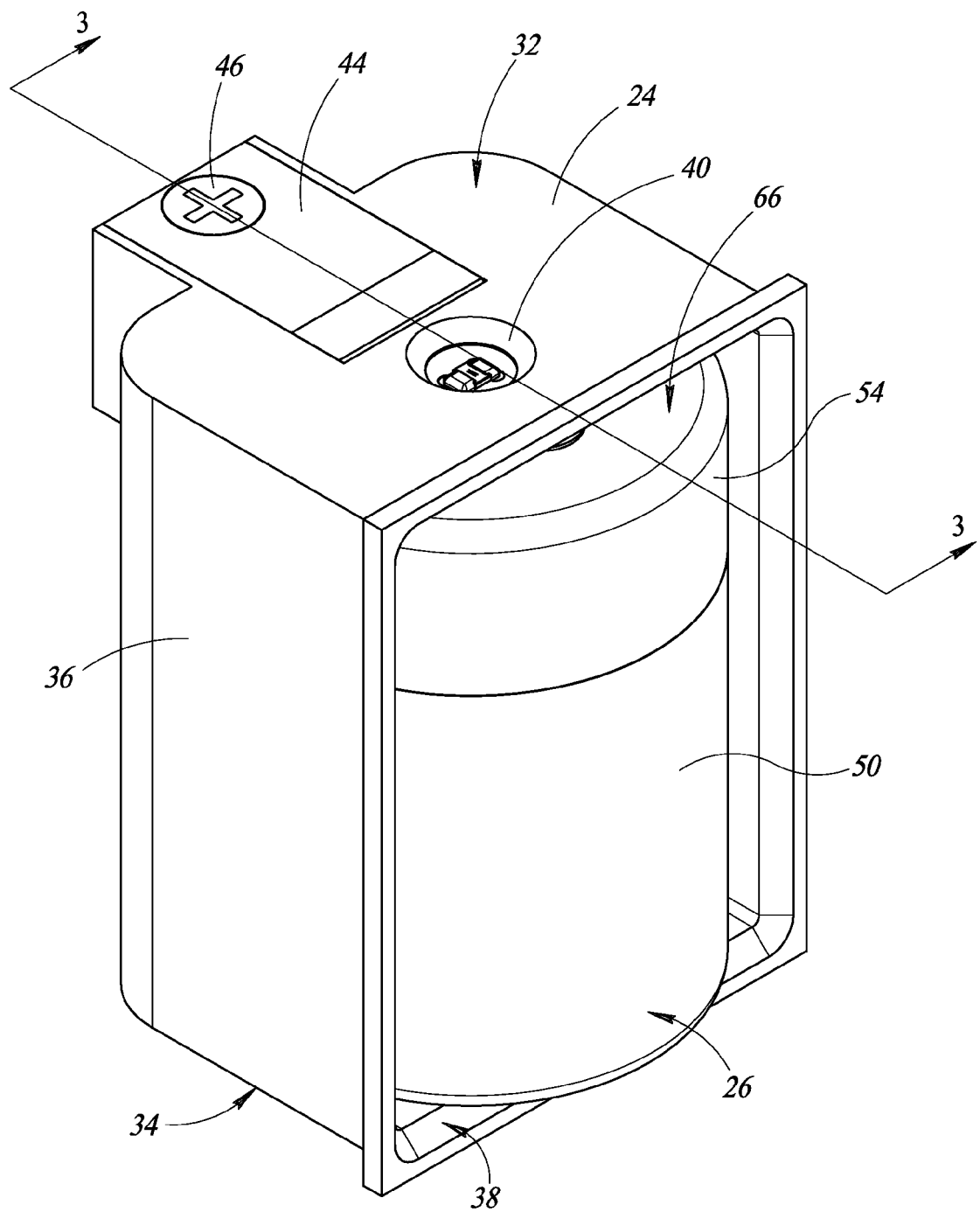
FIGS. 2A-2B are schematic isometric views of a microfluidic refill cartridge and a holder in accordance with one embodiment.
Figure 2B:
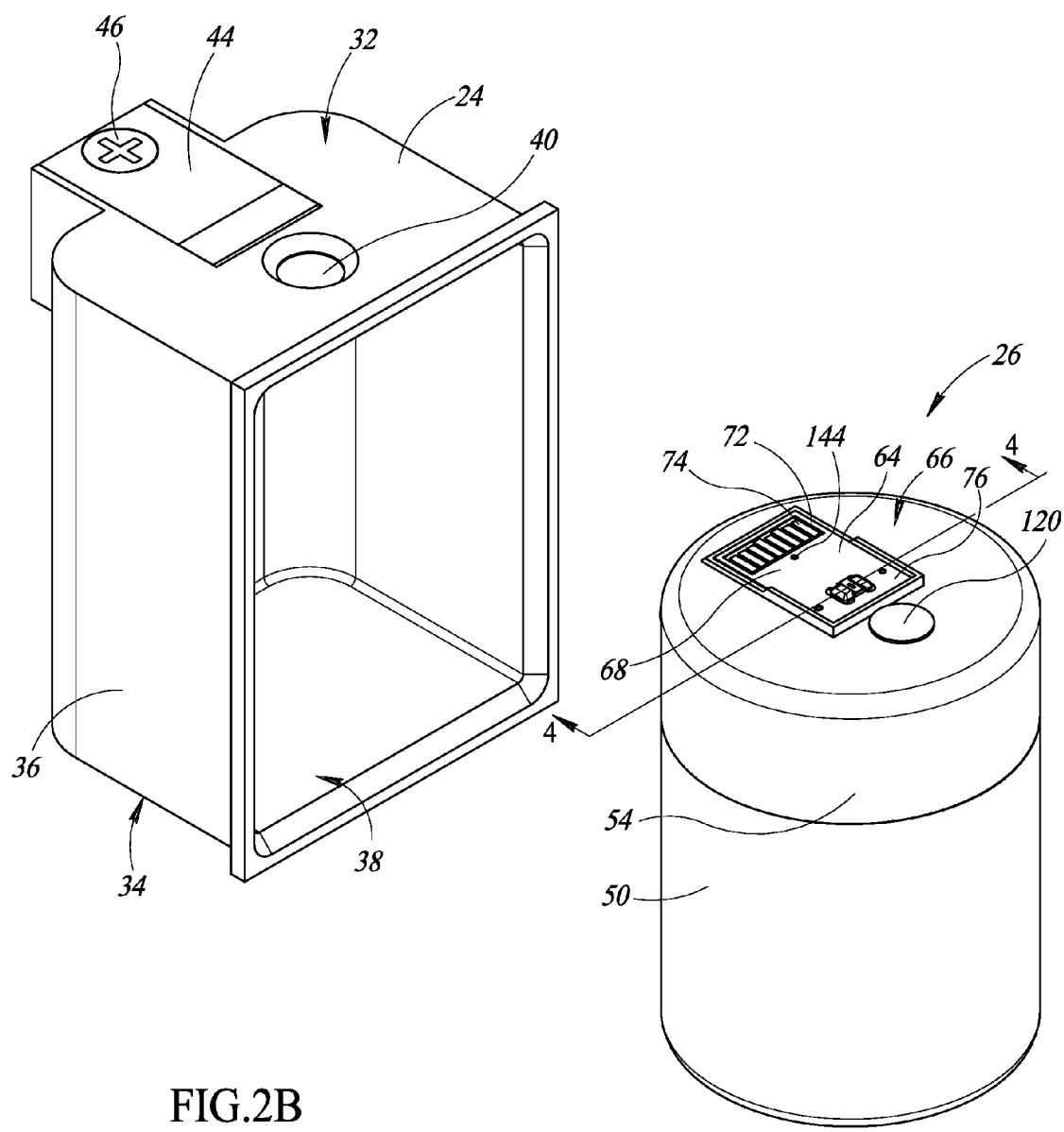

FIG. 2A shows the microfluidic refill cartridge 26 in the holder member 24 without the housing 12, and FIG. 2B shows the microfluidic refill cartridge 26 removed from the holder member 24. A circuit board 44 is coupled to the upper surface 32 of the holder member by a screw 46. As will be explained in more detail below, the circuit board 44 includes electrical contacts 48 (FIG. 3) that electrically couple to contacts of the microfluidic refill cartridge 26 when the cartridge is placed in the holder member. The electrical contacts 48 of the circuit board 44 are in electrical communication with the conductive elements.

Figure 3:
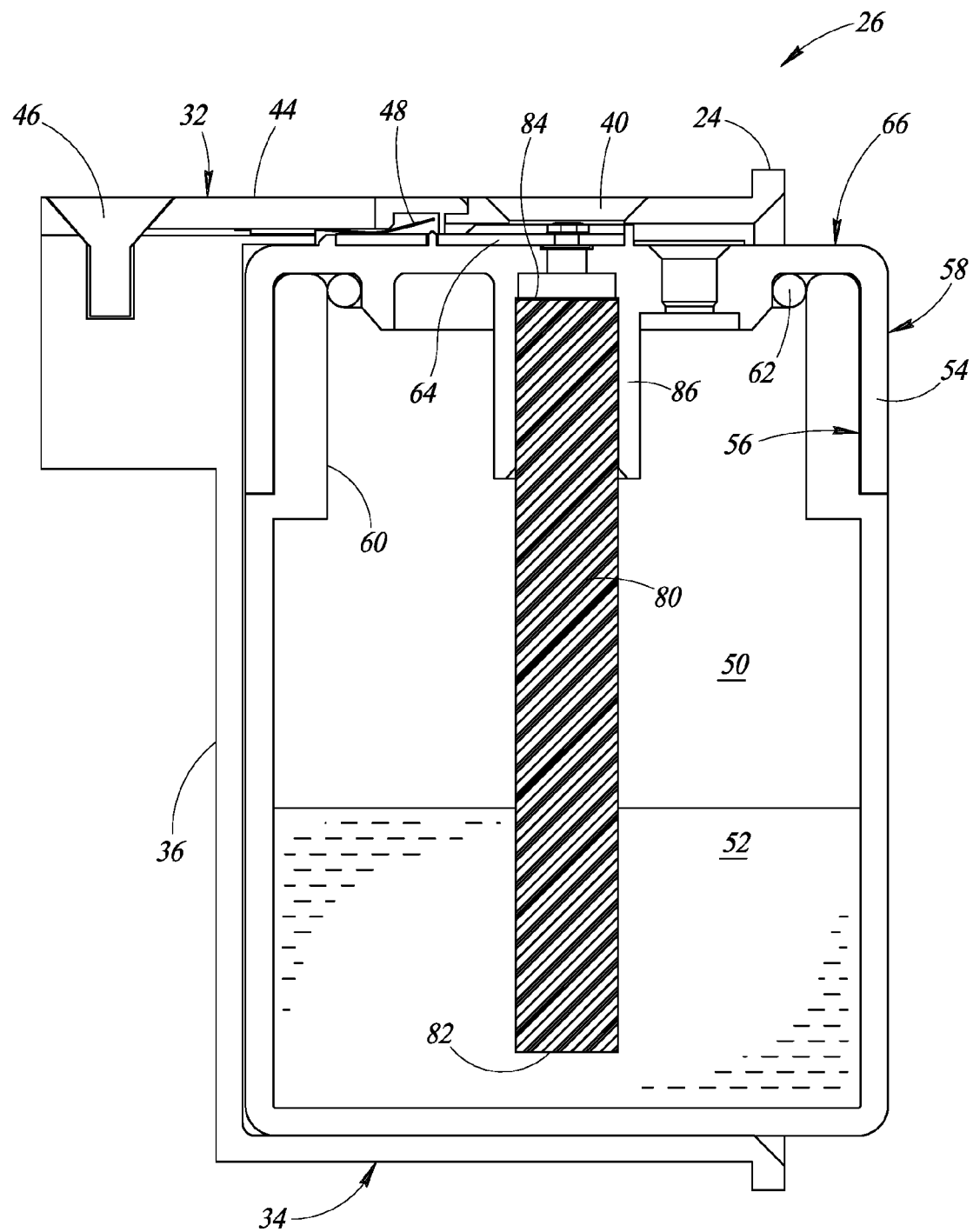
FIG. 3 is a cross-section schematic view of line 3-3 in FIG. 2A.

FIG. 3 is a cross-section view of the microfluidic refill cartridge 26 in the holder member 24 along the line 3-3 shown in FIG. 2A. With reference to FIG. 2B and FIG. 3, the microfluidic refill cartridge 26 includes a reservoir 50 for holding a fluid 52. The reservoir 50 may be any shape, size, or material configured to hold any number of different types of fluid. The fluid held in the reservoir may be any liquid composition. In one embodiment, the fluid is an oil, such as a scented oil. In another embodiment, the fluid is water. It may also be alcohol, a perfume, a biological material, a polymer for 3-D printing, or other fluid.

A lid 54, having an inner surface 56 and an outer surface 58, is secured to an upper portion 60 of the reservoir 50 to cover the reservoir 50. The lid 54 may be secured to the reservoir in a variety of ways known in the art. In some embodiments, the lid 54 is releasably secured to the reservoir 50. For instance, the lid 54 and the upper portion 60 of the reservoir 50 may have corresponding threads, or the lid 54 may snap onto the upper portion 60 of the reservoir 50. Between the lid 54 and the reservoir 50 there may be an O-ring 62 for forming a seal therebetween. The seal may prevent fluid from flowing therethrough as well as prevent evaporation of the fluid to an external environment.

A microfluidic delivery member 64 is secured to an outer surface 66 of the lid 54 of the microfluidic refill cartridge 26 as is best shown in FIG. 2B. The microfluidic delivery member 64 includes an upper surface 68 and a lower surface 70 (see also FIG. 4). A first end 72 of the upper surface 68 includes electrical contacts 74 for coupling with the electrical contacts 48 of the circuit board 44 when placed in the holder member 24. As will be explained in more detail below, a second end 76 of the microfluidic delivery member 64 includes a fluid path for delivering fluid therethrough.

In reference to FIG. 3, inside the reservoir 50 is a fluid transport member 80 that has a first end 82 in the fluid 52 in the reservoir and a second end 84 that is above the fluid 52.

The fluid 52 travels from the first end 82 of the fluid transport member 80 to the second end 84 by capillary action. In that regard, the fluid transport member 80 includes one or more porous materials that allow the fluid to flow by capillary action. The construction of the fluid transport member 80 permits fluid to travel through the fluid transport member 80 against gravity. Fluid can travel by wicking, diffusion, suction, siphon, vacuum, or other mechanism. The second end 84 of the transport member is located below the microfluidic delivery member 64. The fluid transport member 80 delivers fluid 52 from the reservoir 50 toward the microfluidic delivery member 64.

Figure 4:
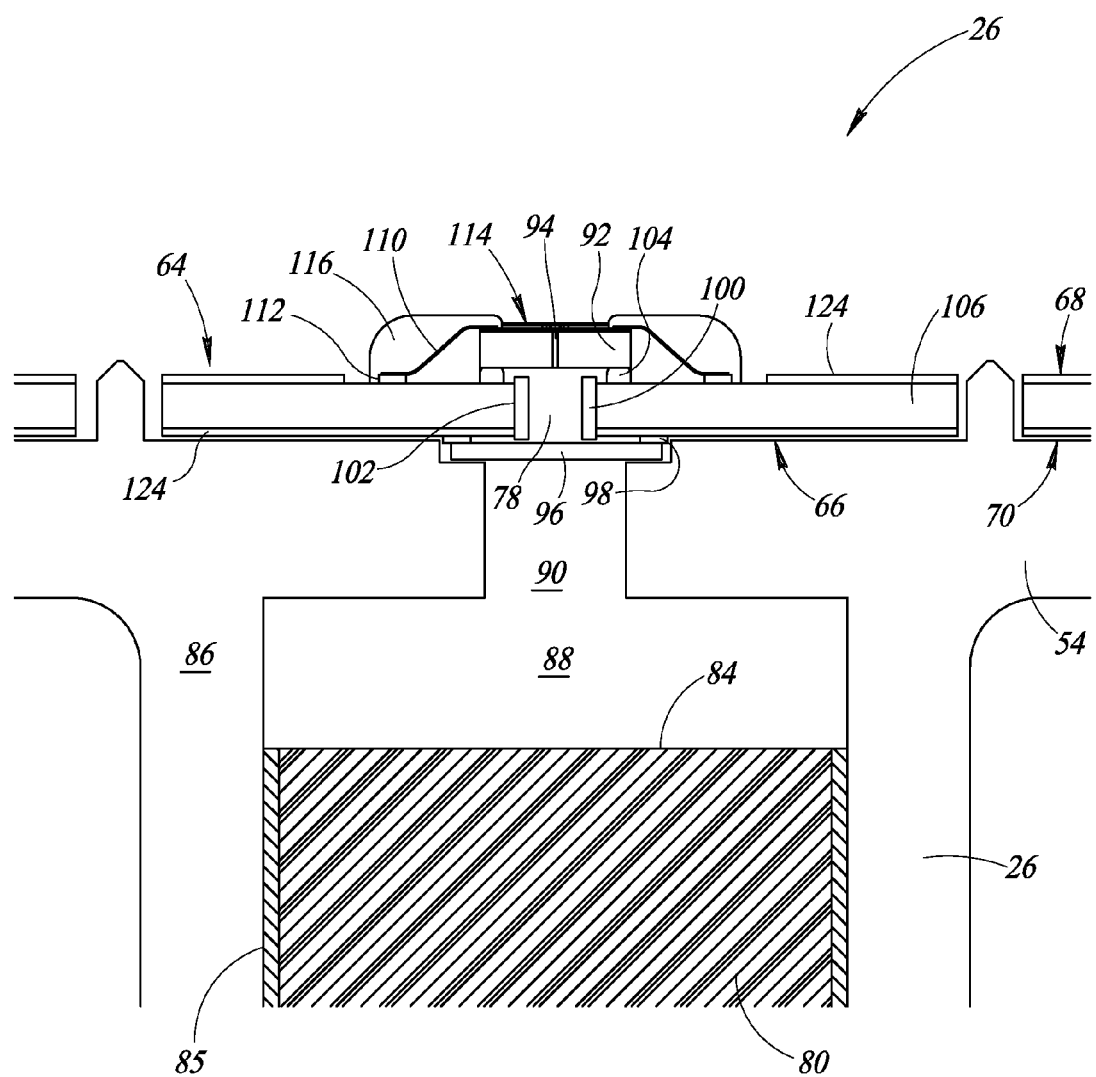
FIG. 4 is a cross-section schematic view of line 4-4 in FIG. 2B.

As best shown in FIG. 4, the second end 84 of the fluid transport member 80 is surrounded by a transport cover 86 that extends from the inner surface of the lid 54. The second end 84 of the fluid transport member 80 and the transport cover 86 form a chamber 88. The chamber 88 may be substantially sealed between the transport cover 86 and the second end 84 of the fluid transport member 80 to prevent air from the reservoir 50 from entering the chamber 88.

Above the chamber 88 is a first through hole 90 in the lid 54 that fluidly couples the chamber 88 above the second end 84 of the fluid transport member 80 to a second through hole 78 of the microfluidic delivery member 64. The microfluidic delivery member 64 is secured to the lid 54 above the first through hole 90 of the lid 54 and receives fluid therefrom.

In some embodiments, the fluid transport member 80 includes a polymer; non-limiting examples include polyethylene (PE), including ultra-high molecular weight polyethylene (UHMW), polyethylene terephthalate (PET), polypropylene (PP), nylon 6 (N6), polyester fibers, ethyl vinyl acetate, polyvinylidene fluoride (PVDF), and polyethersulfone (PES), polytetrafluroethylene (PTFE). The fluid transport member 80 may be in the form of woven fibers or sintered beads. It is also to be appreciated that the fluid transport member of the present disclosure is of smaller size than is typically used for fluid transport members for refillable cartridges.

As shown in FIG. 4, the fluid transport member 80 may include an outer sleeve 85 that surrounds radial surfaces of the fluid transport member 80 along at least a portion of its length while keeping the first and second ends 82, 84 of the fluid transport members 80 exposed. The sleeve 85 may be made from a non-porous material or a material that is less porous than the fluid transport member 80. In that regard, the sleeve 85 may prevent or at least reduce air in the reservoir from entering the fluid transport member 80 by radial flow.

The outer sleeve 85 may be a material that is wrapped around the fluid transport member 80. In other embodiments, the material for the outer sleeve 85 is formed on the fluid transport member 80 in an initial liquid state that dries or sets on the fluid transport member. For instance, the material may be sprayed on the fluid transport member or the fluid transport member may be dipped into a liquid material that dries. The outer sleeve may be a polymer sheet, a Teflon tape, a thin plastic layer, or the like. Teflon tape has particular benefits since it provides a fluid-tight seal, is flexible to wrap, is strong, and also makes it easy to slip member 80 into place.

The fluid transport member 80 may be any shape that is able to deliver fluid 52 from the reservoir 50 to the microfluidic delivery member 64. Although the fluid transport member 80 of the illustrated embodiment has a width dimension, such as diameter, that is significantly smaller than the reservoir, it is to be appreciated that the diameter of the fluid transport member 80 may be larger and in one embodiment substantially fills the reservoir 50.

Figure 5A:
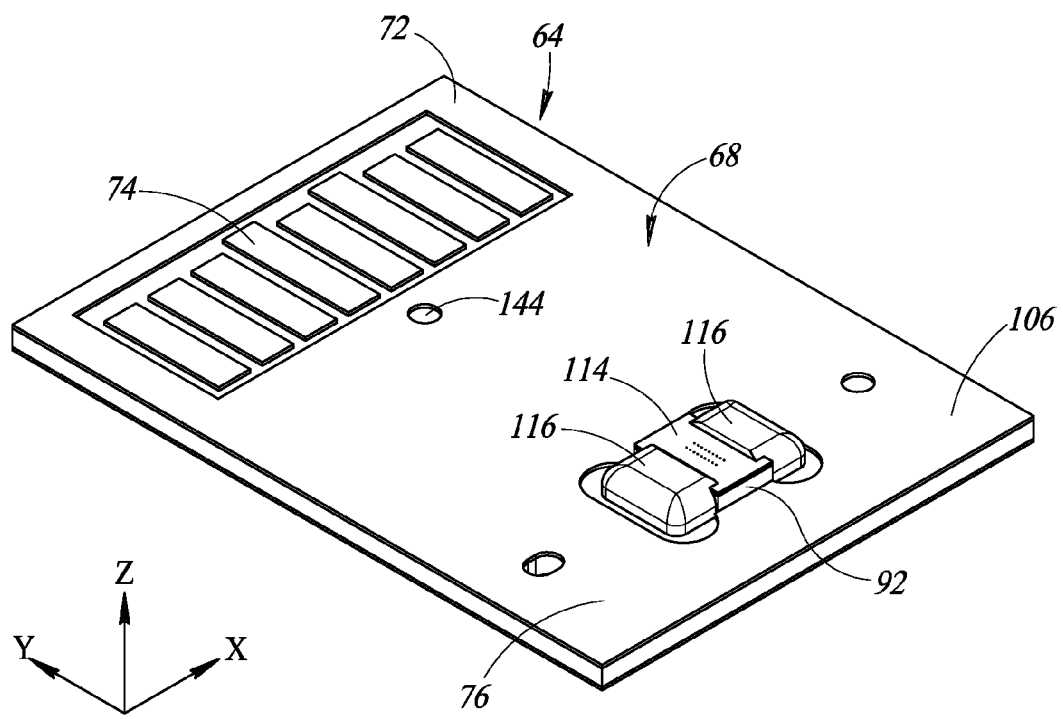
FIGS. 5A-5B are schematic isometric views of a microfluidic delivery member in accordance with an embodiment.
Figure 5B:
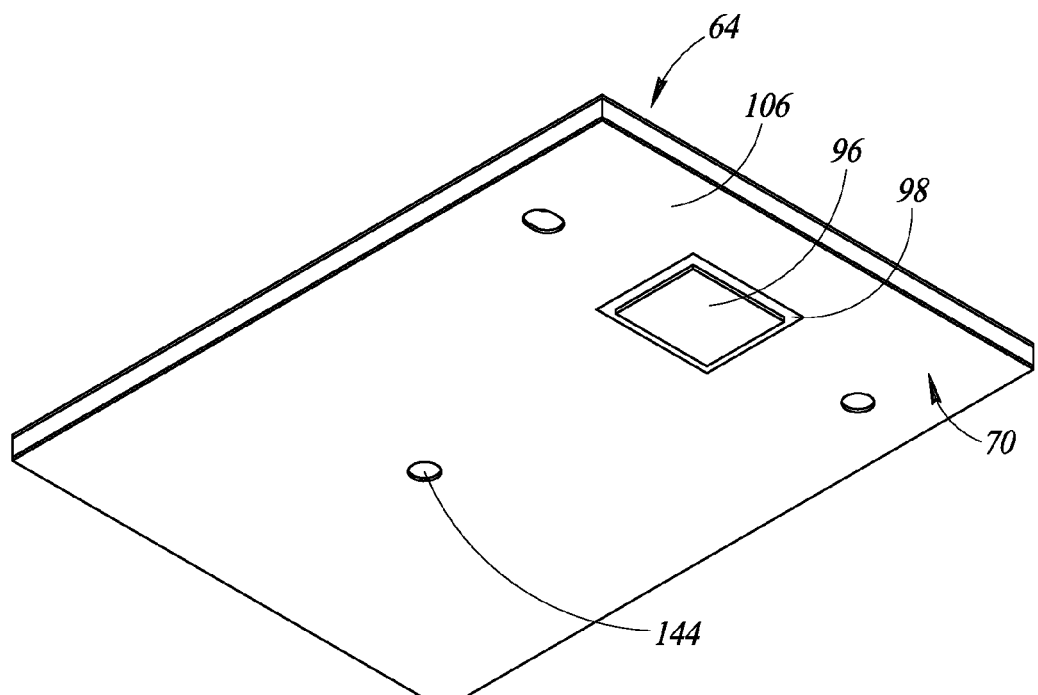
Figure 5C:
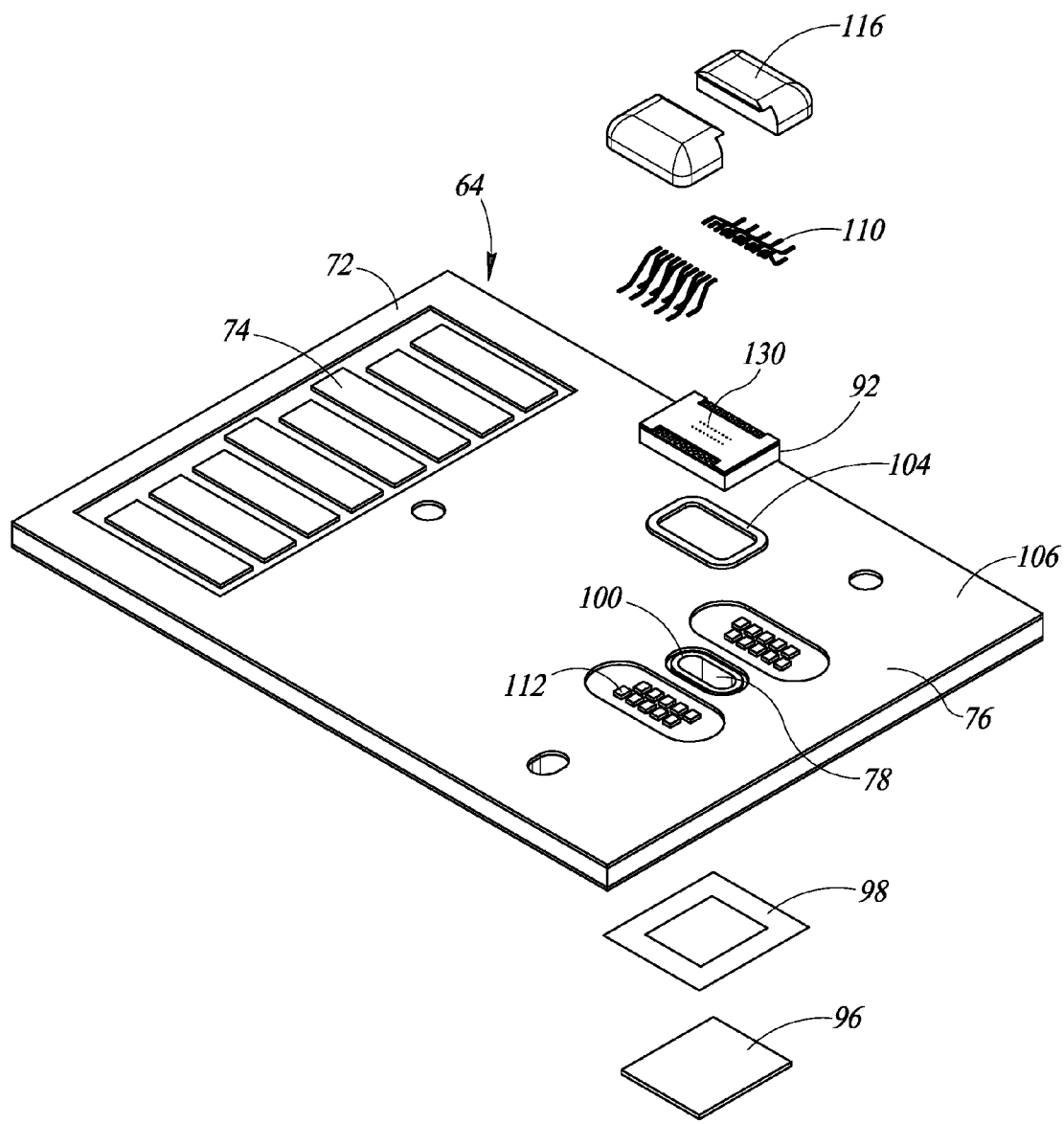
FIG. 5C is an exploded view of the structure in FIG. 5A.

FIGS. 5A and 5B, respectively, are top and bottom views of the microfluidic delivery member 64 in accordance with one embodiment. FIG. 5C illustrates the microfluidic delivery member 64 in exploded view. The microfluidic delivery member 64 includes a rigid planar circuit board, which can be a printed circuit board (PCB) 106 having the upper and lower surfaces 68, 70. The PCB 106 includes one or more layers of insulative and conductive materials as is well known in the art. In one embodiment, the circuit board includes FR4, a composite material composed of woven fiberglass cloth with an epoxy resin binder that is flame resistant. In other embodiments, the circuit board includes ceramic, glass or plastic.

The upper surface 68 of the second end 76 of the printed circuit board 106 includes a semiconductor die 92 above the second through hole 78 and leads 112 located proximate the die 92. Electrical contacts 74 at the first end 72 of the microfluidic delivery member 64 are coupled to one or more of the leads 112 at the second end 76 by electrical traces (not shown).

The upper and lower surfaces 68, 70 of the PCB 106 may be covered with a solder mask 124 as shown in the cross-section view of FIG. 4. Openings in the solder mask 124 may be provided where the leads 112 are positioned on the circuit board or at the first end 72 where the electrical contacts 74 are formed. The solder mask 124 may be used as a protective layer to cover electrical traces.

The die 92 is secured to the upper surface 68 of the printed circuit board 106 by any adhesive material 104 configured to hold the semiconductor die to the PCB. The adhesive material may be an adhesive material that does not readily dissolve by the fluid in the reservoir. In some embodiments, the adhesive material is activated by heat or UV. In some embodiments, a mechanical support (not shown) may be provided between a bottom surface 108 of the die 92 and the upper surface 68 of the printed circuit board 106.

Figure 6:
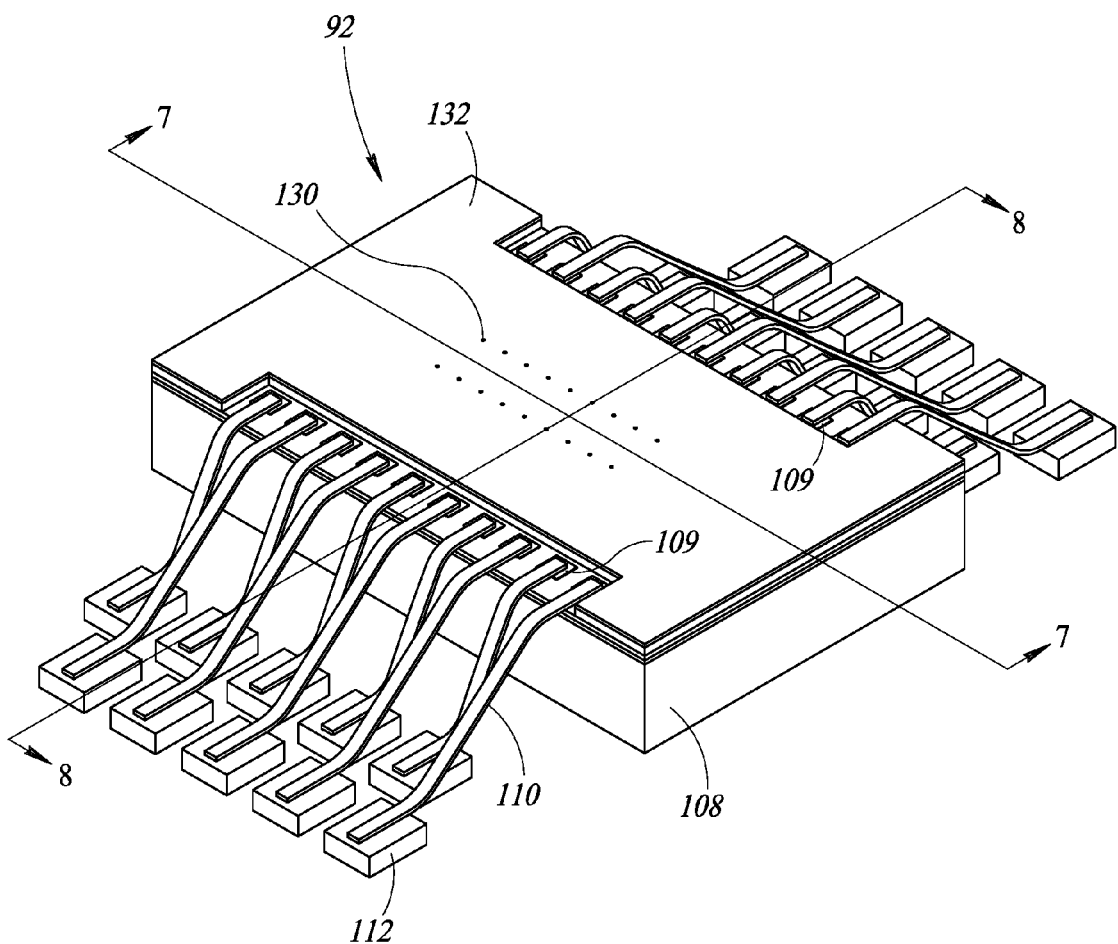
FIG. 6 is a schematic top view of a die in accordance with one embodiment.

As best shown in FIG. 6, the die 92 includes a plurality of bond pads 109 that are electrically coupled to one or more of the leads 112 by conductive wires 110. That is, a first end of the conductive wires 110 is coupled to a respective bond pad 109 of the die 92 and a second end of the conductive wires 110 is coupled to a respective lead 112. Thus, the bond pads 109 of the die 92 are in electrical communication with the electrical contacts 74 of the microfluidic delivery member 64. A molding compound or encapsulation material 116 may be provided over the conductive wires 110, bond pads 109, and leads 112, while leaving a central portion 114 of the die 92 exposed.

Figure 7A:
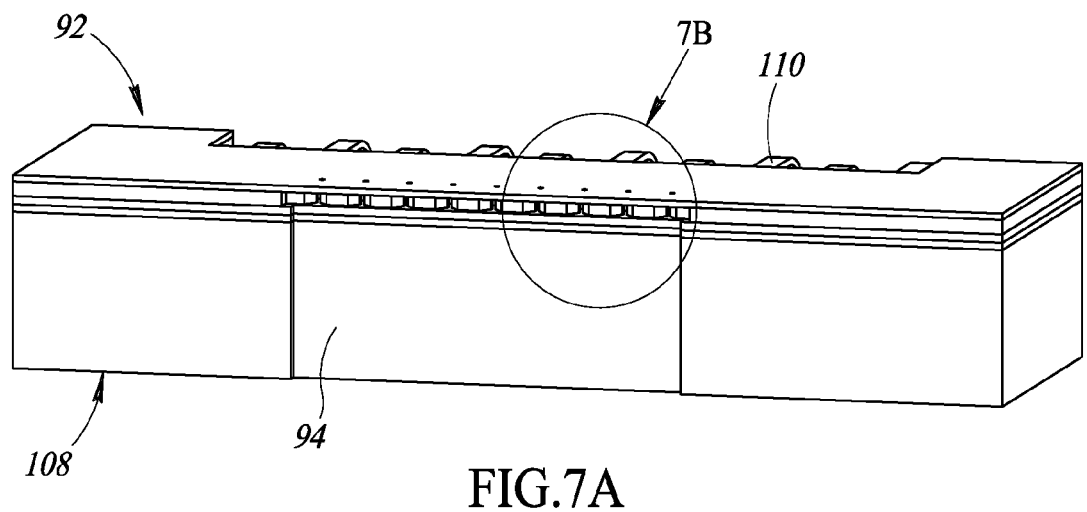
FIG. 7A is a cross-section schematic view of line 7-7 in FIG. 6.
Figure 7B:
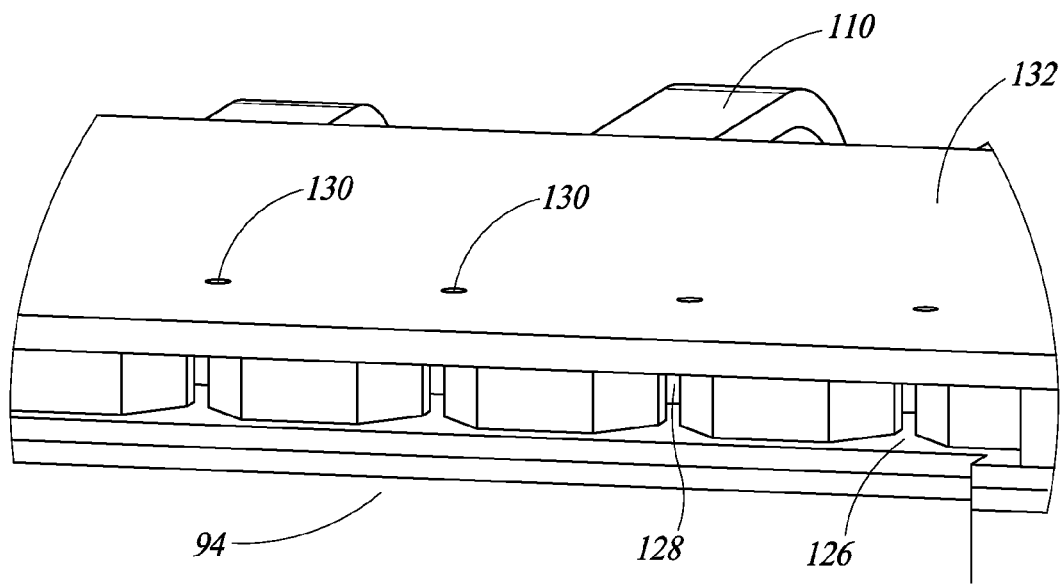
FIG. 7B is an enlarged view of a portion of FIG. 7A.
Figure 8A:
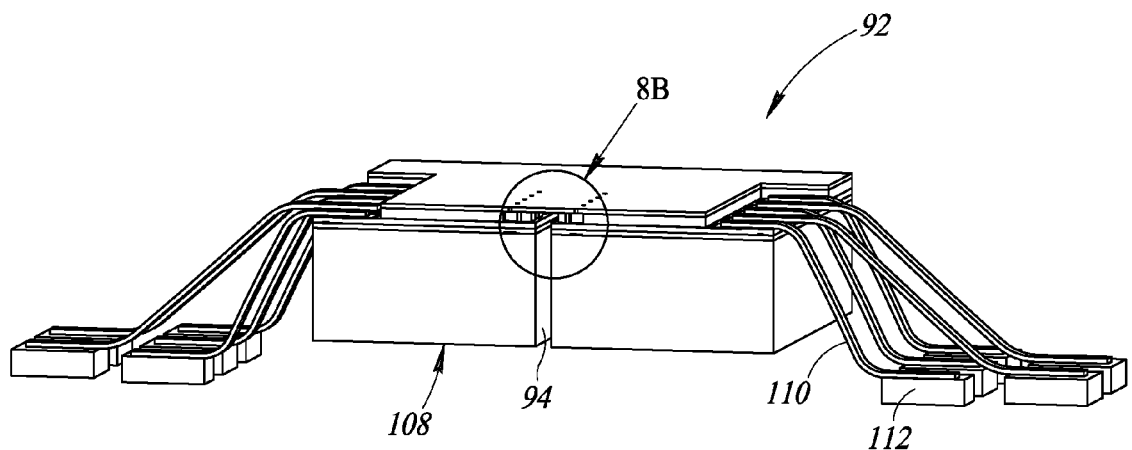
FIG. 8A is a cross-section schematic view of line 8-8 in FIG. 6.

As best shown in FIG. 4, the die 92 includes an inlet path 94 in fluid communication with the second through hole 78 on the second end 76 of the delivery member 64. With reference also to FIGS. 7 and 8, which illustrate corresponding cross sections of the die of FIG. 6, the inlet path 94 of the die 92 is in fluid communication with a channel 126 that is in fluid communication with individual chambers 128 and nozzles 130, forming a fluid path through the die 92. Above the chambers 128 is a nozzle plate 132 that includes the plurality of nozzles 130. In a first embodiment, each nozzle 130 is located above a respective one of the chambers 128 and is an opening in the nozzle plate 132 that is in fluid communication with an environment outside of the microfluidic refill cartridge 26. The die 92 may have any number of chambers 128 and nozzles 130, including one chamber and nozzle. In the illustrated embodiment, the die 92 includes 18 chambers 128 and 18 nozzles 130, each chamber associated with a respective nozzle. Alternatively, it can have 10 nozzles and 2 chambers, one chamber providing fluid for a bank of five nozzles. It is not necessary to have a one-to-one correspondence between the chambers and nozzles. In one embodiment, the nozzle plate 132 is 12 microns thick. In some embodiments, In some embodiments, the nozzle 130 has a diameter between 20-30 microns.

Figure 8B:
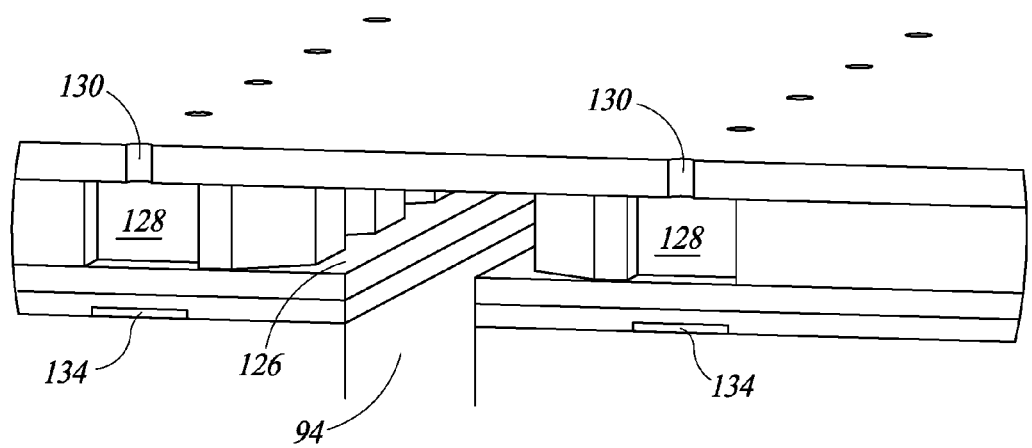
FIG. 8B is an enlarged view of a portion of FIG. 8A.

As is best shown in FIG. 8B, proximate each chamber 128 is a heating element 134 that is electrically coupled to and activated by an electrical signal being provided by a bond pad of the die 92. In use, when the fluid in each of the chambers 128 is heated by the heating element 134, the fluid vaporizes to create a bubble. The expansion that creates the bubble causes a droplet to form and eject from the nozzle 130. Other ejection elements may be used for causing fluid to be ejected from the nozzle 130. For instance, piezoelectric elements or ultrasonic fluid ejection elements may be used to cause fluid to be ejected through the nozzles 130 as is well known in the art. Each nozzle 130 is in fluid communication with the fluid in the reservoir by a fluid path that includes the first end 82 of the fluid transport member 80, through the transport member to the second end 84, the chamber 88 above the second end 84 of the transport member, the first through hole 90 of the lid, the second through hole 78 of the PCB, through the inlet path 94 of the die, through the channel 126, to the chamber 128, and out of the nozzle 130 of the die 92.

In reference again to FIG. 4, a filter 96 may be positioned between the chamber 88 and inlet path 94 of the die 92. The filter 96 is configured to prevent at least some particles from passing therethrough, thereby preventing and/or reducing blockage in the fluid path, most particularly in the nozzles 130 of the die 92. In some embodiments, the filter 96 is configured to block particles that are greater than one third of the diameter of the nozzles.

The filter 96 may be any material that blocks particles from flowing therethrough and does not break apart when exposed to the fluid, which could create further particles to block the fluid path. In one embodiment, the filter 96 is a stainless steel mesh. In other embodiments, the filter 96 is a randomly weaved mesh and may comprise polypropylene or silicon.

Figure 10:
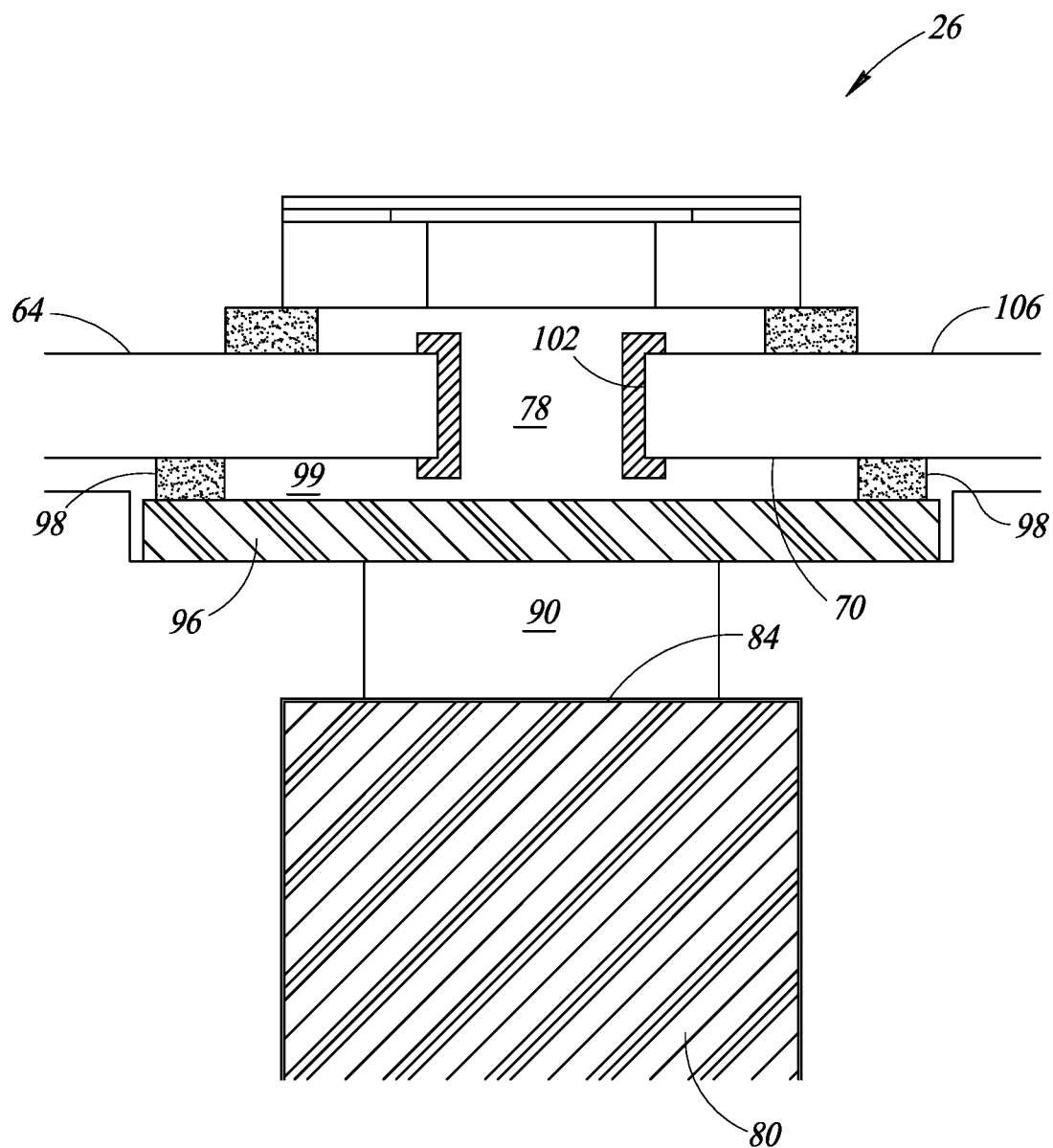
FIG. 10 is a cross-section schematic view of a fluid path of a microfluidic refill cartridge in accordance with one embodiment.

Referring now to FIG. 10, there is provided a close up view of a portion of a microfluidic refill cartridge 26 illustrating a flow path with a filter 96 between the second end 84 of the fluid transport member 80 and the die 92 in accordance with one embodiment.

The filter 96 is separated from the lower surface 70 of the microfluidic delivery member 64 proximate the second through hole 78 by a first mechanical spacer 98. The first mechanical spacer 98 creates a gap 99 between the bottom surface 70 of the microfluidic delivery member 64 and the filter 96 proximate the through hole 78. In that regard, the outlet of the filter 96 is greater than the diameter of the second through hole 78 and is offset therefrom so that a greater surface area of the filter 96 can filter fluid than would be provided if the filter was attached directly to the bottom surface 70 of the microfluidic delivery member 64 without the mechanical spacer 98. It is to be appreciated that the mechanical spacer 98 allows suitable flow rates through the filter. That is, as the filter clogs up with particles, the filter will not slow down the fluid flowing therethrough. In one embodiment, the outlet of the filter is 4 mm$^2$ or larger and the standoff is 700 microns thick.

The first mechanical spacer 98 may be a separate rigid support, a protrusion formed on the lower surface 70 of the microfluidic delivery member 64, such as the solder mask, or adhesive material that conforms to a shape that provides an adequate distance between the filter 96 and the lower surface 70 of the microfluidic delivery member 64. The adhesive material may be an adhesive material that does not readily dissolve by the fluid in the reservoir. In some embodiments, the adhesive material is activated by heat or UV. The adhesive material may be the same or different from the adhesive material used to secure the die to the microfluidic delivery member.

It is to be appreciated that in some embodiments, the fluid transport member 80 is made from one or more materials that do not react with the fluid. Thus, the fluid transport member 80 does not introduce contaminants into the fluid that could block fluid flow through the microfluidic delivery member 64. In one embodiment, the fluid transport member 80 may replace the filter, so that a separate filter 96 is not needed.

As shown in FIG. 10, the second through hole 78 of the microfluidic delivery member 80 may include a liner 100 that covers exposed sidewalls 102 of the PCB 106. The liner 100 may be any material configured to protect the PCB from breaking apart, such as to prevent fibers of the PCB from separating. In that regard, the liner 100 may protect against particles from the PCB 106 entering into the fluid path and blocking the nozzles 130. For instance, the second through hole 78 may be lined with a material that is less reactive to the fluid in the reservoir than the material of the PCB. In that regard, the PCB may be protected as the fluid passes therethrough. In one embodiment, the through hole is coated with a metal material, such as gold.

Prior to use, the microfluidic refill cartridge 26 may be primed to remove air from the fluid path. During priming, air in the fluid path is replaced with fluid from the reservoir 50. In particular, fluid may be pulled up from the fluid transport member 80 to fill the chamber 88, the first through hole 90 of the lid 54, the second through hole 78 of the microfluidic delivery member 64, the inlet path 94 of the die 92, the channel 126, and the chamber 128. Priming may be performed by applying a vacuum force through the nozzles 130. The vacuum force is typically performed with the microfluidic refill cartridge in an upright position for a few seconds. In some embodiments, a vacuum force is applied for 30 to 60 seconds. The microfluidic refill cartridge 26 may also be primed by applying air pressure through a hole 140 (FIG. 9) in the lid 54 of the cartridge that is in fluid communication with the reservoir 50 to increase the air pressure on the fluid in the reservoir 50, thereby pushing fluid up the fluid transport member 80 through the fluid path. It is to be appreciated that the hole is sealed with a cover 120 (see FIG. 2B), such as elastic material that fits into at least a portion of the hole, after priming.

Once primed, the nozzles 130 may be sealed to prevent de-priming of the fluid path. De-priming may occur when air enters the fluid path. In that regard, a cover (not shown) may be placed over the nozzles 130 to prevent air from outside of the microfluidic refill cartridge 26 from entering the fluid path. It is to be appreciated that in some embodiments, the outer sleeve 85 of the fluid transport member 80 may prevent de-priming of the fluid transport member 80. That is, the sleeve 85 prevents air from entering the fluid transport member 80 along its radial surface.

Once primed, during use, when fluid exits the nozzle 130, fluid from the reservoir 50 is pulled up through the fluid path by capillary action. In that regard, as fluid exits the chamber 128, fluid automatically refills the chamber 128 by being pulled through the fluid path by capillary action.

As indicated above, the transport cover 86 in combination with the second end 84 of the fluid transport member 80 form a seal that fluidly isolates the chamber 88 from the reservoir 50 to assist in keeping the microfluidic refill cartridge 26 primed. It is to be appreciated that the chamber 88 may be at a different pressure than the reservoir 50.

It is to be appreciated that in many embodiments, the fluid transport member 80 is configured to self-prime. That is, fluid may travel from the first end 82 of the fluid transport member 80 to the second end 84 without the aid of a vacuum force or air pressure as discussed above.

The microfluidic refill cartridge 26 includes a vent path that places the reservoir in fluid communication with the external environment of the microfluidic refill cartridge 26. The vent path equalizes the air pressure in the reservoir 50 with the air pressure of the external environment. That is, as fluid exits the microfluidic refill cartridge 26 through the nozzles 130, air from the external environment fills the space in the reservoir 50 that is made by the removed fluid. In that regard, the air pressure above the fluid in the reservoir remains at atmosphere. This allows the microfluidic refill cartridge to remain primed and prevents or at least reduces back pressure in the fluid path. That is, by equalizing the pressure in the reservoir, the reservoir does not create a vacuum that pulls the fluid from the fluid path back into the reservoir.

Figure 9:
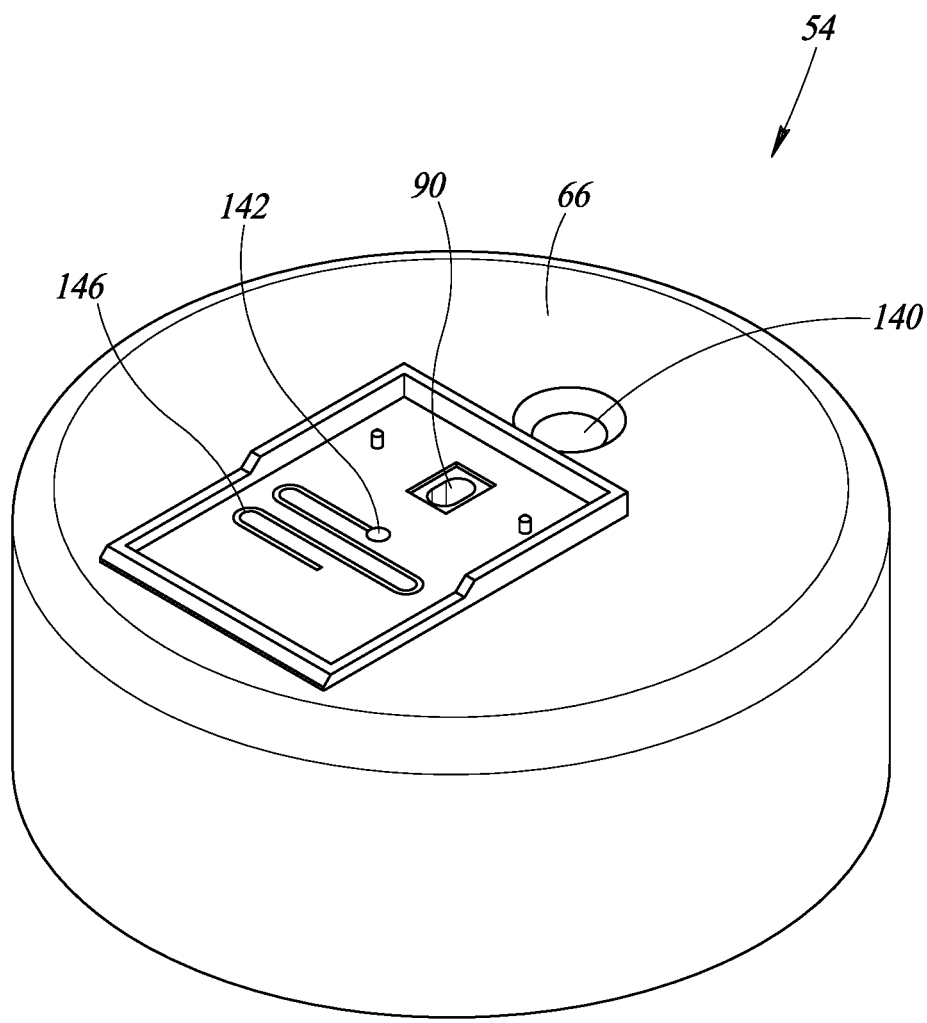
FIG. 9 is a schematic top view of the lid of the microfluidic refill cartridge without the microfluidic delivery member in accordance with one embodiment.

Referring now to FIG. 9, the vent path includes a first vent hole 142 in the lid 54 of the microfluidic refill cartridge and a second vent hole 144 in the microfluidic delivery member 64 (See FIGS. 5A and 5B). The first and second vent holes 142, 144 are not aligned with each other but are in fluid communication with each other by a channel 146 formed in the outer surface 66 of the lid 54. It is to be appreciated that in another embodiment, the lower surface 70 of the microfluidic delivery member 64 could alternatively or additionally include a channel that places the first vent hole 142 in fluid communication with the second vent hole 144. It is to be appreciated that separating the first vent hole 142 from the second vent hole 144 by the channel 146 reduces the evaporation rate of the fluid in the reservoir 50 through the vent path.

Upon depletion of the fluid in the reservoir 50, the microfluidic refill cartridge 26 may be removed from the housing 10 and replaced with another microfluidic refill cartridge 26. Alternatively, the microfluidic refill cartridge 26 may be refilled through the hole 140 in the lid 54 as best shown in FIG. 9.

Figure 11A:
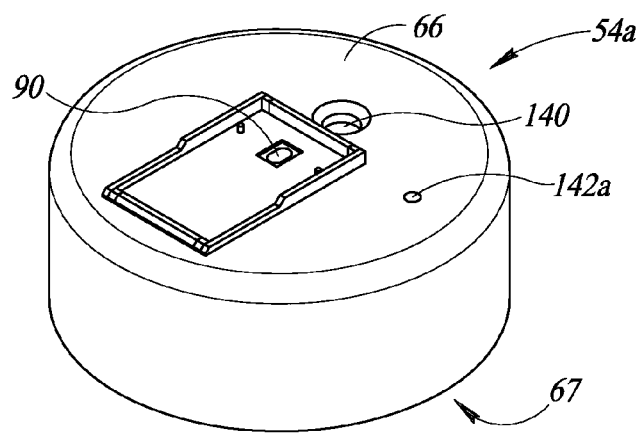
FIGS. 11A-11D are schematic views of a lid and vent hole in accordance with one embodiment.
Figure 11B:
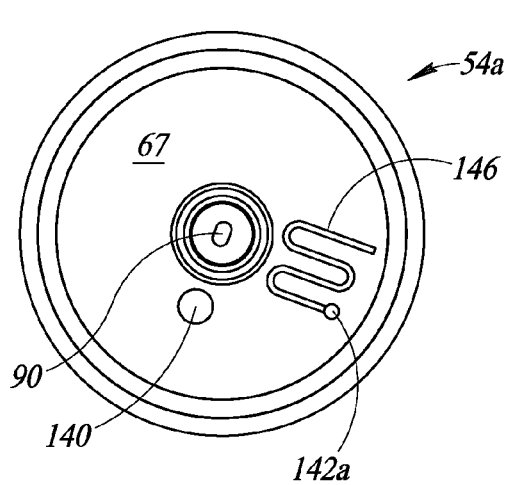
Figure 11C:
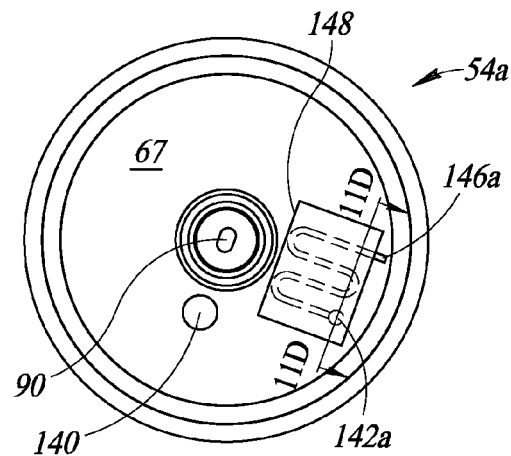
Figure 11D:
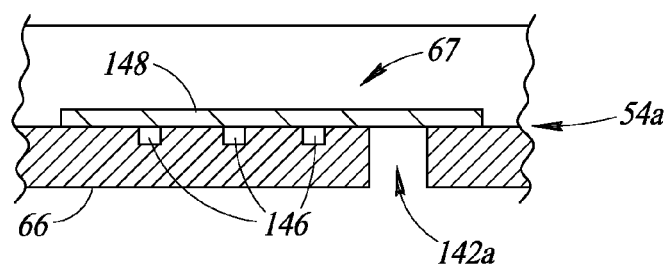

FIGS. 11A-11D illustrate schematic views of a lid 54a that may be used with the microfluidic refill cartridge 26 in accordance with another embodiment. FIG. 11A is an isometric outer view of the lid 54a. FIGS. 11B and 11C illustrate inner views of the lid 54a, with FIG. 11B illustrating the inner surface 67 of lid 54a without cover 148 and FIG. 11C illustrating the inner surface 67 of the lid 54a with the cover 148. FIG. 11D is a cross-section view of the lid 54a of FIG. 11C.

The lid 54a of FIGS. 11A-11D is substantially the same in structure and function to the lid 54 described and shown in relation to FIGS. 1-10 and, thus, only differences will be described in the interest of brevity. Generally described, the lid 54a differs from the lid 54 of FIG. 9 in that the vent path is different and provided at a different location of the lid.

As mentioned above, the vent path equalizes the air pressure in the reservoir 50 with the air pressure of the external environment. The vent path of FIGS. 11A-11D includes a vent hole 142a and a channel 146 formed in an inner surface 67 of the lid 54a. The vent path places air in the reservoir 50 in fluid communication with an environment external thereto through the end portion 146a that is exposed to the air in the reservoir 50, through the channel 146, and to the vent hole 142a that is open to the external environment. The channel 146 may be in a serpentine shape as shown or any other shape.

As shown in FIGS. 11C and 11D, over at least a portion of the channel 146 and the vent hole 142a is a cover 148. In particular, the cover 148 covers the vent hole 142a and most of the channel 146, but leaves an end portion 146a of the channel 146 open so that the reservoir 50 is in fluid communication with the channel when the lid 54a is coupled to the reservoir 50. In FIG. 11B, the cover 148 is removed exposing the channel 146. In FIG. 11C, the cover 148 is located over the channel 146 and the vent hole 142a, thus, these features are shown in dashed lines.

The cover 148 may be any material suitable for covering the channel 146. In one embodiment, the cover 148 is a film that is coupled to the inner surface 67 of the lid 54a. The cover 148 may be coupled to the inner surface 67 of the lid 54a by adhesive material that couples the cover 148 to the inner surface 67 of the lid 54a. Alternatively, the cover 148 may be formed from a polymer resin that adheres to the inner surface 67 of the lid 54a in response to heat being applied thereto. Due to the vent path having a covered channel 146 that couples an end portion 146a of the channel 146 to the vent hole 142a, the vent path slows evaporation of the fluid in the reservoir 50. That is, by having the end portion 146a open to the air in the reservoir 50 and the vent hole 142 open to the external environment, the evaporation rate of the fluid in the reservoir 50 is slowed in that the fluid, to evaporate from the reservoir, must travel through the channel 146 that is covered by the cover 148.

Although the channel 146 is formed on the inner surface 67 of the lid 54a in the illustrated embodiment, the channel 146 may be formed on the outer surface 66 of the lid 54a. In such an embodiment one end of the channel 146 is in fluid communication with air in the reservoir 50 and the other end of the channel 146 is in fluid communication with the external environment. In this embodiment, the cover 48 would be located on the outer surface 66 of the lid 54a over the channel 146.

Figure 12A:
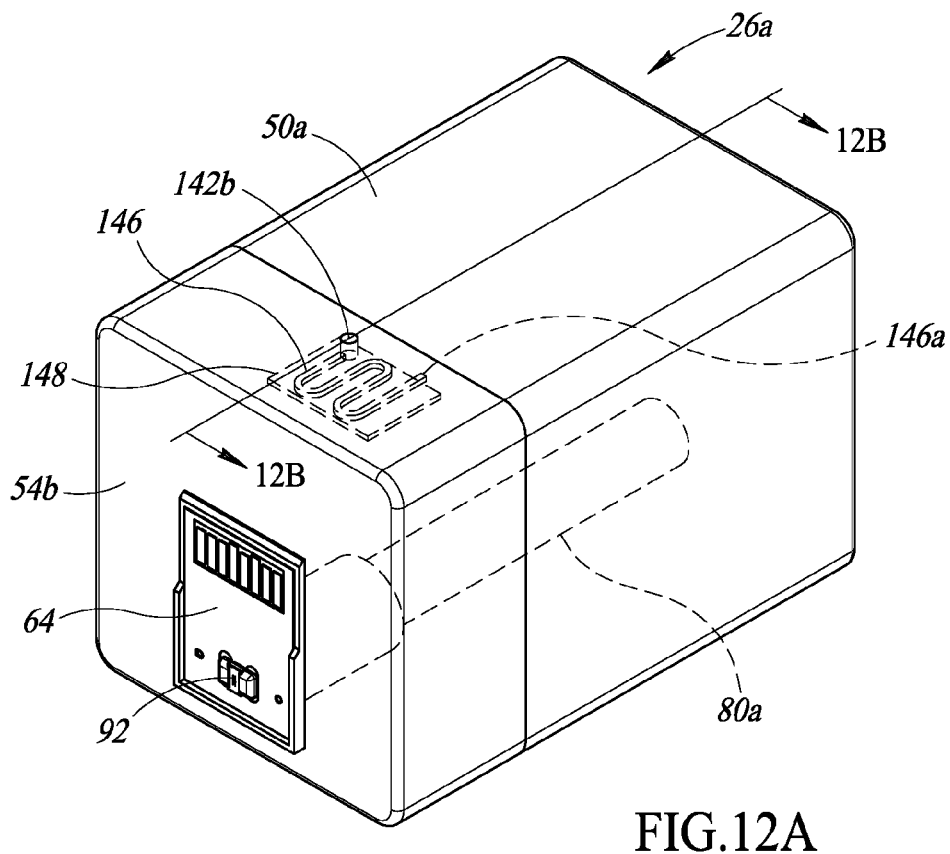
FIGS. 12A and 12B are schematic views of a microfluidic refill cartridge in accordance with another embodiment.
Figure 12B:
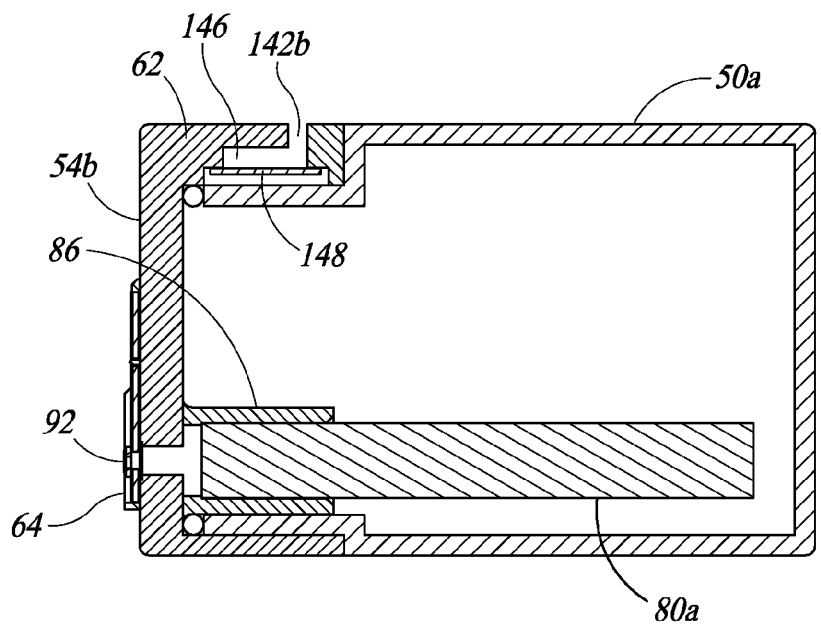

FIGS. 12A and 12B are directed to a microfluidic refill cartridge 26a in accordance with another embodiment. The microfluidic refill cartridge 26a of FIGS. 12A and 12B is substantially the same in structure and function to microfluidic refill cartridge 26 described and shown in relation to FIGS. 1-10 and, thus, only differences will be described in the interest of brevity. Generally described, the microfluidic refill cartridge 26a of FIGS. 12A and 12B differs from the microfluidic refill cartridge 26 of the above figures in that the microfluidic refill cartridge 26a is orientated in a horizontal position rather than in the vertical position. In that regard, the vent path of the microfluidic refill cartridge 26a is located on a side surface of the microfluidic refill cartridge 26a so that air in the reservoir 50a can equalize with the air external to the microfluidic refill cartridge 26a.

The microfluidic refill cartridge 26a, which includes a lid 54b coupled to the reservoir 50a, may have a shape suitable for being in horizontal position, such as the rectangular shape shown. The microfluidic refill cartridge 26a may be inserted in the holder member 24, thus a round shaped microfluidic refill cartridge 26 may also be used. Thus, the microfluidic refill cartridge 26a may have any suitable shape.

The vent path is located on a side surface of the microfluidic refill cartridge 26a. In the illustrated embodiment, the vent path is located on the upward facing side surface of the lid 54a. However, it is to be appreciated that the vent path may also be located on the side surface of the reservoir 50a. The vent path includes a similar shape and structure of the vent path shown and described in reference to FIGS. 11A-11D. Thus, only differences will be discussed in the interest of brevity.

The vent path of FIGS. 12A and 12B differs from the vent path of FIGS. 1A-11D in that the vent path is located in the side of the lid 54b rather than in the top of the lid 54b. In particular, the side of the lid 54b includes a vent hole 142b that extends through the entire thickness of the side of the lid. An inner portion of the upper side of the lid 54b includes the channel 146 as shown in dashed line in FIG. 12A and cross section in FIG. 12B. The channel 146 has a serpentine shape. The cover 148 is coupled to the inner surface of the side surface of the lid 54b to cover the vent hole 142b and the channel 146. An end 146a of channel 146 that is opposite the vent hole remains uncovered by the cover 148. The end 146a of the channel 146 is also uncovered by the reservoir 50a when the reservoir 50a is coupled to the lid 54b so that the end of the channel is in fluid communication with the fluid in the reservoir 50a. Thus, the reservoir 50a may have a through hole at the location of the end 146a of the channel 146.

Alternatively, the reservoir 50a itself forms the lid 54b that covers the channel 146 and the opening in the lid 54b exposes the end 146a of the channel 146.

In view of the horizontal position, the fluid transport member 80a is located proximate a side surface 81 of the reservoir 50a that is opposite the vent path during operation of the microfluidic refill cartridge 26a. In that regard, the fluid transport member 80a remains in the fluid as the fluid in the reservoir 50a goes down. Furthermore, the microfluidic delivery member 64 is located on the lid 54b proximate the side surface 81 of the microfluidic refill cartridge 26a. In that regard, the fluid in the reservoir travels through the fluid transport member 80a to the left in FIG. 12B of the microfluidic delivery member 64. It is to be appreciated that in general the fluid travels through the fluid transport member 80a to the semiconductor die 92 of the microfluidic delivery member 64, as described above in reference to the vertical position. The fluid transport member 80a may be shorter than shown so long as the fluid transport member 80a is located in the fluid in the reservoir 50a.

Due to the fluid transport member 80a being sideways, the fluid transport member 80a may be made from a different material from the fluid transport member 80a of the embodiments with the microfluidic refill cartridge 26 in the vertical position. In general, the material selected for the fluid transport member 80a will depend on the fluid to be used in the reservoir 50a. That is, the fluid transport member 80a material will depend on the viscosity and surface tension of the fluid to be used in the reservoir 50a. For instance, the fluid transport member 80a may include one or more materials that provide suitable back pressure for the fluid to be used in the reservoir 50a. In some embodiments, the fluid is an oil based fluid or a water based fluid. Materials for the fluid transport member that can provide back pressure for fluids with lower surface tension and/or lower viscosity include sponges, foam, and compressed filters. When fluids with greater surface tension and/or greater viscosity are to be used, materials for the fluid transport member as described in the embodiments of the vertical position may be used in operation with this horizontal orientation. Furthermore, when fluids with greater surface tension and/or greater viscosity are to be used, a vent path may include only the air vent without the channel and the cover.

Although not shown, the microfluidic refill cartridge 26a may be received by a holder member 24 as described above in reference to FIGS. 1-2B. As will be clear to a person of ordinary skill in the art, the holder member would include an inner portion configured to receive the shape of the microfluidic refill cartridge 26a. As will be clear to a person of ordinary skill in the art, an end of the holder member proximate the circuit board 44 would include an opening to expose the microfluidic delivery member 64 to the external environment. In that regard, the holder member used in conjunction with this embodiment may have a different shape than shown in reference to FIGS. 1-2B.

Figure 13A:
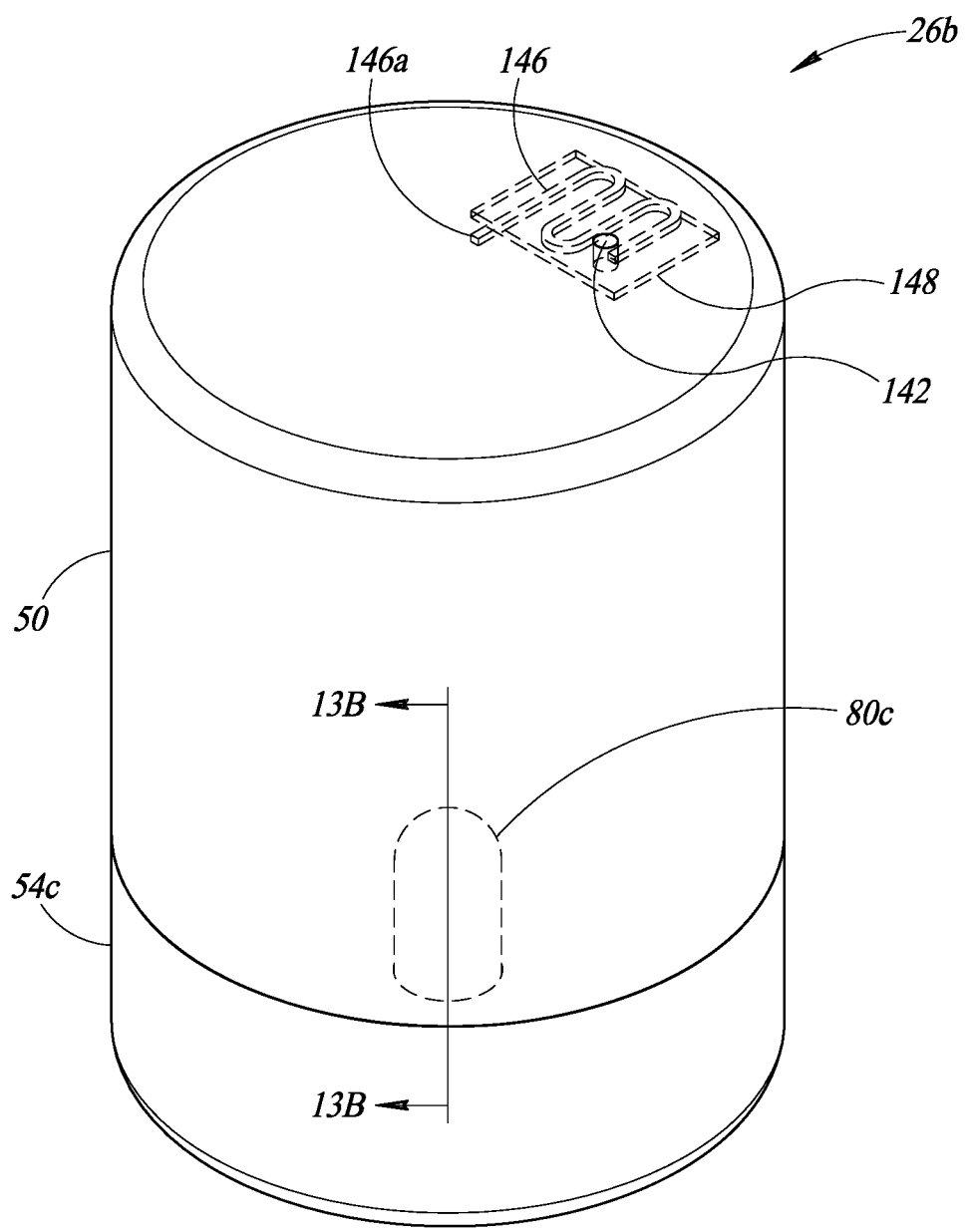
FIGS. 13A and 13B are schematic views of another microfluidic refill cartridge in accordance with yet another embodiment.
Figure 13B:
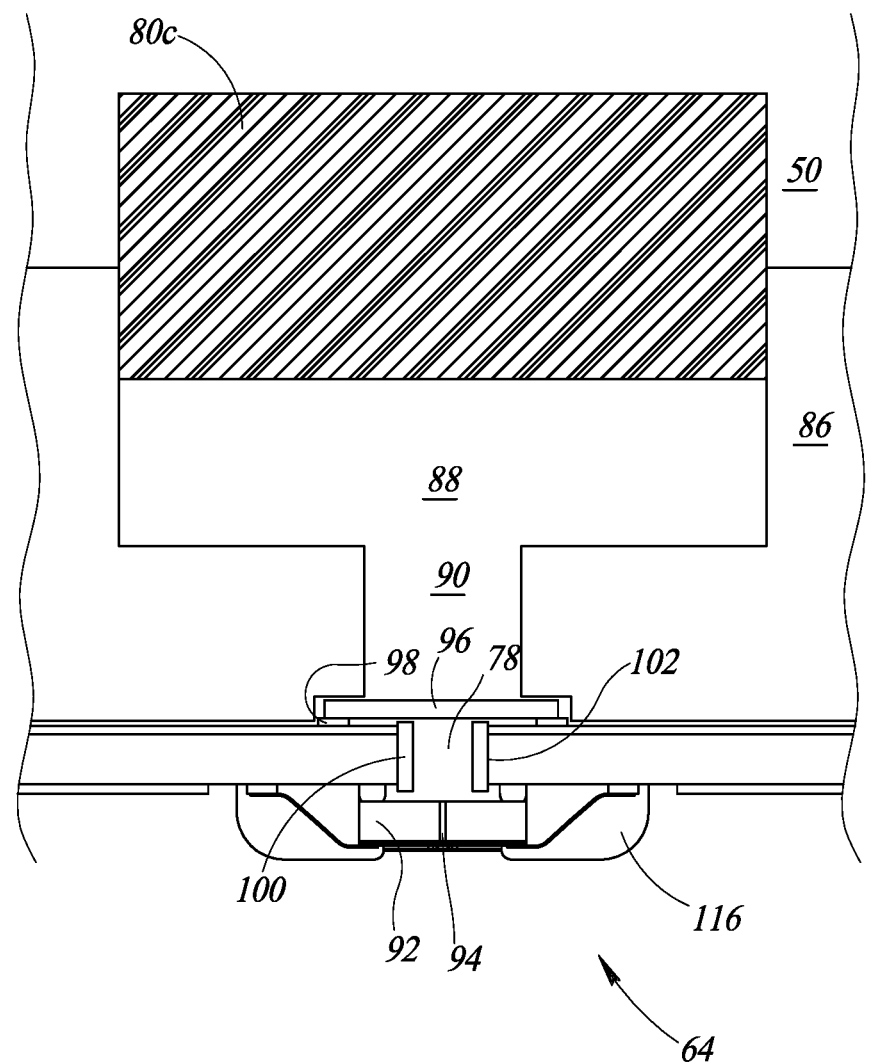

FIGS. 13A and 13B are directed to a microfluidic refill cartridge 26b in accordance with yet another embodiment. FIG. 13A illustrates a bottom isometric view of the microfluidic refill cartridge 26b, while FIG. 13B is a cross-section view of a portion of the microfluidic refill cartridge 26b of FIG. 13A. The microfluidic refill cartridge 26b is substantially the same in structure and function to microfluidic refill cartridge 26 described and shown in relation to FIGS. 1-10 and, thus, only differences will be described in the interest of brevity. Generally described, the difference between the microfluidic refill cartridge 26b and the microfluidic cartridge 26 is that the microfluidic refill cartridge 26b is in an upside down position. In the upside down position, the vent path is located on an end of the reservoir 50 of the microfluidic refill cartridge 26b. The vent path, however, may instead be located on a side surface of the reservoir proximate the end.

The vent path is similar in structure and function to the vent path described above in reference to FIGS. 11A and 11D and thus will not be repeated again in the interested of brevity. Generally described, the vent path differs from the vent path of FIGS. 11A-11D in that the vent path is formed in an end of the reservoir 50 rather than in the lid 54c. That is, the channel 146 is formed on a surface of the end of the reservoir 50 and the vent hole 142 is a through hole extending through the end of the reservoir 50. The cover 148 is coupled to the inner surface of the end of the reservoir 50 covering the vent hole 142 and the channel 146, while an end 146a of the channel remains uncovered to place the channel 146 in fluid communication with the air the end of the reservoir 50.

The microfluidic refill cartridge 26b also includes a fluid transport member 80c, shown in dashed line, that is smaller than the fluid transport member 80 described in references to the prior embodiments. Thus, as the fluid in the reservoir 50 goes down during operation of the microfluidic refill cartridge 26b, the end of the fluid transport member 80c continues to receive the fluid that remains in the reservoir 50. The length of the fluid transport member 80c shown in the image is merely illustrative and would likely be smaller than shown. Although not shown, the microfluidic refill cartridge 26a is received by a holder member 24 in the upside down position.

Figure 14A:
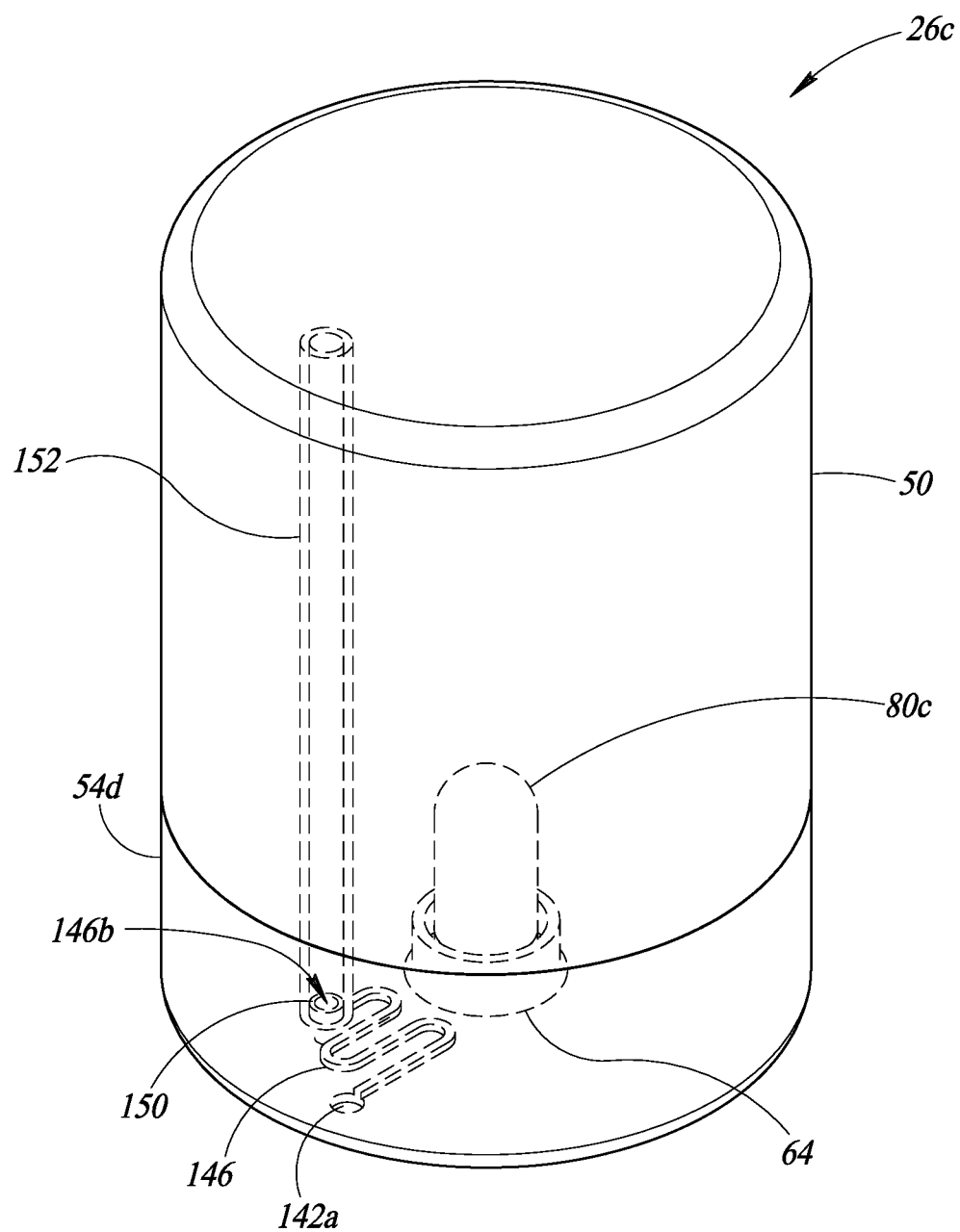
FIGS. 14A-14C are schematic views of another microfluidic refill cartridge in accordance with yet another embodiment.
Figure 14B:
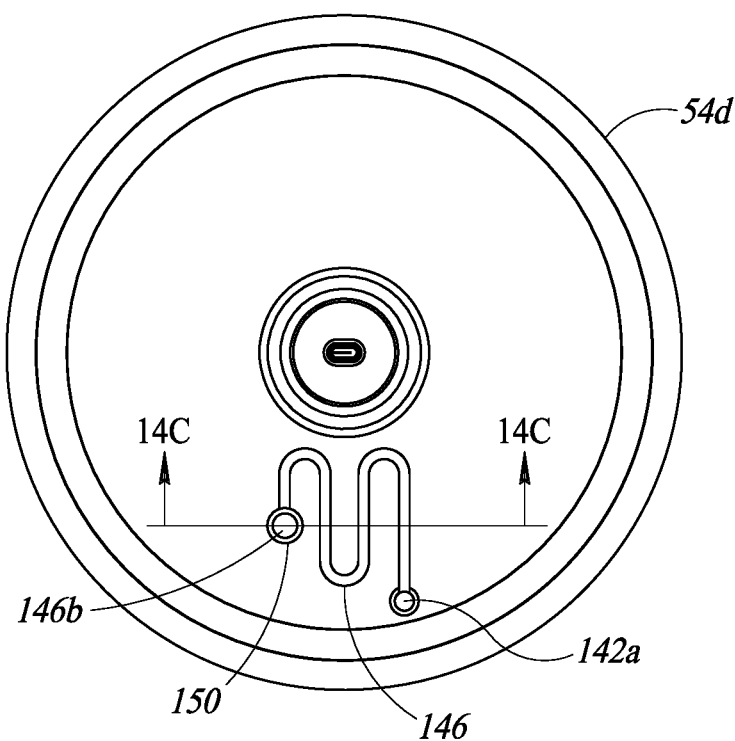
Figure 14C:
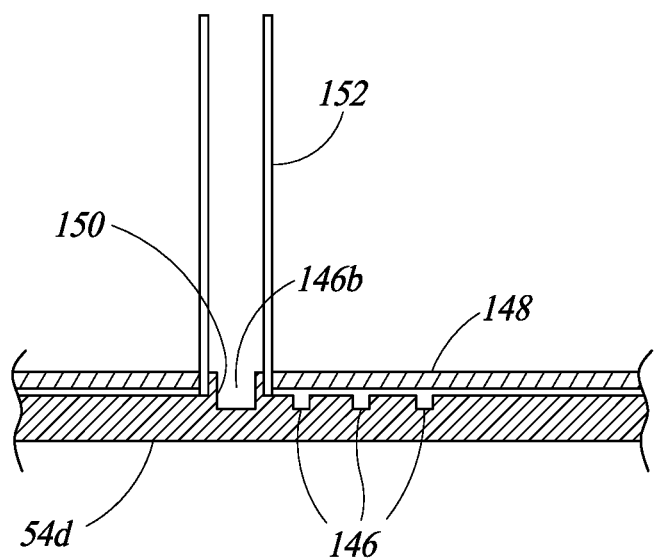

FIGS. 14A-14C are directed to a microfluidic refill cartridge 26c in accordance with yet another embodiment. FIG. 14A is bottom isometric view of the microfluidic refill cartridge 26c. FIG. 14B is a bottom view of the lid 54d without the reservoir 50. FIG. 14C is a partial cross-section view of the lid 54d illustrating the vent path.

The microfluidic refill cartridge 26c has substantially the same structure and function as the microfluidic refill cartridge 26b of FIGS. 13A and 13B and, thus, only differences will be described in the interest of brevity. Generally described, the difference between the microfluidic refill cartridge 26c of FIGS. 14A-14C and the microfluidic refill cartridge 26b of FIGS. 13A and 13B is that the microfluidic refill cartridge 26c of FIGS. 14A-14C has the vent path in a lid 54d in the upside down configuration. Thus, the vent path further includes a tube 152 that places the air inside of the reservoir in fluid communication with the air external to the microfluidic refill cartridge 26c.

In particular, the vent path includes a vent hole 142a that extends through the entire thickness of the lid 54d, a channel 146 on the inner surface of the lid 54d, a cover 148 (shown in FIG. 14C) over the channel 146, with an end 146b of the channel 146 exposed. The end 146b of the channel 146 is not exposed to the fluid. Rather, the end 146b of the channel 146 includes an annular portion 150 at the end 146b of the channel that is configured to couple with the tube 152. The cover 148 may cover the entire inner surface of the lid 54d except for the end 146b of the channel 146.

In the illustrated embodiment, the tube 152 slips over the annular portion 150, however the tube 152 may also slip into the annular portion 150. Thus, the vent path includes the through opening 142a, the channel 146, the end 146b of the channel 146, the annular portion 50, and the tube 152.

It is to be appreciated that further embodiments include a microfluidic refill cartridge 26 in other orientations that shown. Furthermore, as indicated above, any of the above embodiments may be modified so that the channel of the vent path is on an outer surface of the lid or the reservoir. Furthermore, the vent path may include any configuration that includes a channel placing air in the reservoir in fluid communication with the external environment.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microfluidic delivery system, comprising:
   a lid;
   a first chamber facing a fluid transport member, the first chamber being configured to receive fluid from an end of the fluid transport member;
   a printed circuit board coupled to the lid and having a through opening in fluid communication with the first chamber;
   a semiconductor die mounted on the printed circuit board covering the through opening, the semiconductor die including:
      a plurality of second chambers in fluid communication with the first chamber and configured to receive the fluid from the first chamber through the through opening in the printed circuit board;
      a plurality of nozzles in fluid communication with the plurality of second chambers; and
      a plurality of ejection elements associated with the plurality of second chambers, each of the plurality of ejection elements being configured to cause the fluid in the plurality of second chambers to be expelled through the plurality of nozzles.

2. The microfluidic delivery system of claim 1, wherein the semiconductor die is arranged below the printed circuit board and the first chamber.

3. The microfluidic delivery system of claim 2, wherein, after fluid exits the plurality of nozzles, the plurality of second chambers refill with fluid to due capillary action and gravity.

4. The microfluidic delivery system of claim 2, wherein the plurality of nozzles are sized so that the fluid does not expel through the plurality of nozzles until ejection elements cause the fluid to be expelled through the plurality of nozzles.

5. The microfluidic delivery system of claim 1, wherein the semiconductor die is arranged above the printed circuit board and the first chamber.

6. The microfluidic delivery system of claim 5, wherein when the fluid that is expelled through the plurality of nozzles, the fluid travels with a trajectory that includes a vertical component in opposition to gravity.

7. The microfluidic delivery system of claim 6, wherein after fluid exits the plurality of nozzles, the plurality of second chambers refill with fluid in a fluid path by capillary action.

8. The microfluidic delivery system of claim 1, wherein the semiconductor die is arranged horizontally relative to the printed circuit board and the first chamber.

9. The microfluidic delivery system of claim 8, wherein when the fluid is expelled through the plurality of nozzles, the fluid travels with a trajectory that includes a horizontal component.

10. The microfluidic delivery system of claim 1, wherein the plurality of ejection elements are heating elements configured to heat the fluid in the second chambers creating a vapor bubble that causes fluid to be ejected through the nozzles.

11. A microfluidic delivery system, comprising:
a lid configured to be secured to a reservoir;
a first through hole in the lid, a first end of the first through hole in fluid communication with the reservoir and configured to receive fluid from an end of a fluid transport member located in the reservoir;
a vent hole in the lid, the vent hole being in fluid communication with air in the reservoir; and
a microfluidic delivery member coupled to the lid, the microfluidic delivery member including:
a circuit board located on the lid and having a second through hole covering the first through hole in the lid; and
a semiconductor die coupled to the circuit board and covering the second through hole, the semiconductor die including:
a plurality of second chambers in fluid communication with the first through hole in the lid and the second through hole in the circuit board;
a plurality of nozzles in fluid communication with the plurality of second chambers; and
a plurality of ejection elements associated with the plurality of second chambers, each of the ejection elements being configured to cause the fluid in the plurality of second chambers to be expelled through the plurality of nozzles.

12. The microfluidic delivery system of claim 11, wherein the lid includes a planar portion and a side portion that extend from the planar portion, wherein the first through hole is in the planar portion of the lid and the vent hole is in the side portion of the lid.

13. The microfluidic delivery system of claim 12, wherein the lid further includes a channel in the side portion of the lid, the channel being in fluid communication with the vent hole and with air in the reservoir.

14. The microfluidic delivery system of claim 13, wherein the channel has a serpentine shape.

15. The microfluidic delivery system of claim 13, further comprising a cover over a portion of the channel and the vent hole.

16. The microfluidic delivery system of claim 11, wherein the lid includes a planar portion and a side portion that extends from the planar portion, wherein the first and vent holes are in the planar portion of the lid.

17. The microfluidic delivery system of claim 16, wherein the lid further includes a channel in the planar portion of the lid, the channel being in fluid communication with the vent hole and with air in the reservoir.

18. The microfluidic delivery system of claim 17, wherein the channel has a serpentine shape.

19. The microfluidic delivery system of claim 17, wherein the channel is located on a surface of the planar portion that faces the reservoir.

20. The microfluidic delivery system of claim 17, further comprising a cover over a portion of the channel and the vent hole.

21. The microfluidic delivery system of claim 17, further comprising a tube having a channel in fluid communication with the vent hole to place the vent hole in fluid communication with the air in the reservoir.

22. A microfluidic delivery system, comprising:
a lid including:
a planar portion having first and second surfaces;
a first through hole in the planar portion, the first through hole configured to be in fluid communication with a fluid in a reservoir; and
a vent hole in the planar portion, the vent hole configured to be in communication with air in the reservoir when the lid is coupled to the reservoir;
a circuit board located on the planar portion and having a second through hole that faces the first through hole in the planar portion; and
a semiconductor die coupled to the circuit board covering the second through hole, the semiconductor die including a nozzle plate having a plurality of nozzles that are configured to eject fluid received from the reservoir through the second through hole of the circuit board.

23. The microfluidic delivery system of claim 22, further comprising a channel on a surface of a side, the channel being in fluid communication with the vent hole.

24. The microfluidic delivery system of claim 23, further comprising a cover over a portion of the channel and the vent hole.

25. The microfluidic delivery system of claim 23, wherein channel is serpentine shaped.

26. A microfluidic delivery system, comprising:
a lid including:
a planar portion and a side portion extending from the planar portion;
a first through hole in the planar portion, the first through hole configured to be in fluid communication with a fluid in a reservoir; and
a vent hole in the lid, the vent hole configured to be in communication with air in the reservoir when the lid is coupled to the reservoir;

a circuit board located on the planar portion and having second through hole that faces the first through hole in the planar portion; and a semiconductor die coupled to the circuit board covering the second through hole, the semiconductor die including a nozzle plate having a plurality of nozzles that are configured to eject fluid received from the reservoir through the second through hole of the circuit board.

27. The microfluidic delivery system of claim 26, further comprising a channel on a surface of in the lid, the channel being in fluid communication with the vent hole.

28. The microfluidic delivery system of claim 27, further comprising a cover over a portion of the channel and the vent hole.

29. The microfluidic delivery system of claim 27, wherein the channel is serpentine shaped.

\* \* \* \* \*

UNITED STATES PATENT AND TRADEMARK OFFICE
CERTIFICATE OF CORRECTION

PATENT NO. : 9,968,700 B2  
APPLICATION NO. : 14/975200  
DATED : May 15, 2018  
INVENTOR(S) : Simon Dodd et al.

Page 1 of 1

It is certified that error appears in the above-identified patent and that said Letters Patent is hereby corrected as shown below:

In the Claims

Column 15, Claim 26, Line 2:
"second through hole that faces the first through hole in" should read, --a second through hole that faces the first through hole in--.

Signed and Sealed this
Eleventh Day of June, 2019

Andrei Iancu
*Director of the United States Patent and Trademark Office*